United States Patent [19]
Peffly et al.

[11] Patent Number: 5,972,356
[45] Date of Patent: Oct. 26, 1999

[54] PERSONAL CARE COMPOSITIONS

[75] Inventors: Marjorie Mossman Peffly, Cincinnati; Raymond Edward Bolich, Jr., Maineville; Kenneth W. Rigney, Cincinnati, all of Ohio

[73] Assignee: The Procter & Gamble Company, Cincinnati, Ohio

[21] Appl. No.: 08/964,648

[22] Filed: Nov. 5, 1997

[51] Int. Cl.$^6$ ............................... A61K 6/00; A61K 7/00; A61K 7/06
[52] U.S. Cl. ................. 424/401; 424/70.1; 424/70.12
[58] Field of Search ................................. 424/401, 70.1, 424/70.12

[56] References Cited

U.S. PATENT DOCUMENTS 3,928,558  12/1975  Cheeseman et al. .................... 424/47
5,658,557   8/1997  Bolich, Jr. et al. .................. 424/70.12

Primary Examiner—Thurman K. Page
Assistant Examiner—Sharon Howard
Attorney, Agent, or Firm—Joan B. Tucker; Stephen T. Murphy; Loretta J. Henderson

[57] ABSTRACT

The present invention relates to personal care compositions suitable for styling hair, comprising from about 0.01% to about 20% of a hair styling polymer, a polyorganosiloxane emulsion comprising a polyorganosiloxane dispersed as particles an average particle size of less than about 150 nanometers, and a surfactant system; from about 0.01% to about 10% of a silicone-polyoxyalkylene copolymer surfactant and a carrier comprising at least about 0.5% of a first solvent selected from the group consisting of water; water soluble organic solvents; organic solvents which are strongly to moderately strong in hydrogen-bonding parameter; and mixtures thereof; wherein the first solvent is other than a $C_1$–$C_3$ monohydric alcohol, a $C_1$–$C_3$ ketone and a $C_1$–$C_3$ ether.

34 Claims, No Drawings

PERSONAL CARE COMPOSITIONS

TECHNICAL FIELD

The present invention relates to hair styling compositions containing silicone emulsions, and corresponding applications of such compositions. The invention further relates to stable, hair styling compositions containing a silicone emulsion and lower monohydric alcohol.

BACKGROUND OF THE INVENTION

The desire to have the hair retain a particular style or shape is widely held. The most common methodology for accomplishing this is by spraying a composition, typically from a mechanical pump spray device or from a pressurized aerosol canister, to the hair. Other means of providing style or shaping to the hair are mousses, gels, lotions and the like. Such compositions provide temporary setting benefits and can usually be removed by water or by shampooing. The materials used in these types of hair styling compositions are generally resins, gums, and adhesive polymers which are capable of imparting style or shape to the hair. Many of these products also contain lower alcohols in order to obtain good films of the polymer in a short period of time.

Many people desire a high level of style retention, or hold, from a styling product. Unfortunately, most current hair styling products having good hold characteristics suffer from the disadvantages of being either too stiff, not smooth or too sticky upon drying. Stiff compositions tend to be brittle and break down under common stresses such as wind, brushing, combing. Stiff compositions also tend to feel and look unnatural. Sticky compositions overcome many of the foregoing disadvantages of stiff compositions, because sticky compositions tend to be more forgiving, i.e., flexible, under stress and allow for restyling of the hair. However, sticky compositions have the disadvantage of leaving the hair with a heavy, coated feel and with a limp and unattractive appearance. Also, sticky compositions cause the hair to quickly become soiled from common contaminant sources such as dust, dirt, lint, sebum, etc.

One approach to minimizing stiffness and roughness of a hair styling composition is the incorporation of silicones, including silicone emulsions and microemulsions, in such compositions. Silicones tend to provide a desirably smooth or soft hair feel. Unfortunately, silicone emulsions tend to be difficult to formulate in hair styling compositions. Hair styling compositions tend to be complex, requiring a number of ingredients for different purposes, with potential for incompatibilities. For example, silicone emulsions tend to be unstable in compositions containing lower alcohols, resulting in phase separation of the composition. Other incompatibilities in the system, e.g., polymer—polymer or polymer-surfactant interactions, can also result in phase separation. This phase separation is not only undesirable for visual esthetic reasons, but for performance reasons as well. When the product phase separates, hold and/or hair feel properties of the product tend to be negatively impacted.

Therefore, a need exists for hair styling compositions providing good style retention without the disadvantages of stiff or sticky compositions. There is a particular need for hair styling compositions containing lower alcohols providing good style retention without the disadvantages of stiff or sticky compositions.

It has surprisingly been found that stable hair styling compositions which provide such benefits can be provided by employing specific silicone polyether compounds in a hair care composition containing a hair styling polymer, a silicone emulsion having a particle size less than about 150 nm and a surfactant, and certain carriers for the hair styling polymer. Such compositions are provided even where the composition contains relatively high levels of lower alcohols.

It is therefore an object of this invention to provide stable hair styling compositions containing silicone emulsions, especially compositions which also contain lower alcohol.

It is another object of this invention to provide hair styling compositions that provide good style retention without unacceptable stiffness or stickiness. Another object of this invention is to provide hair styling compositions that both look and feel natural.

It is another object of this invention to provide methods for styling and holding hair.

These and other objects will become readily apparent from the detailed description which follows.

SUMMARY OF THE INVENTION

The present invention relates to personal care compositions, especially such compositions which are suitable for styling hair. The compositions comprise:

a) from about 0.01% to about 20% of a hair styling polymer;

b) a polyorganosiloxane emulsion comprising:
  (i) a polyorganosiloxane dispersed as particles in the emulsion, the polyorganosiloxane having an average particle size of less than about 150 nm, and
  (ii) a surfactant system for dispersing the organopolysiloxane in the emulsion; wherein the amount of emulsion is such that the personal care composition comprises from about 0.01% to about 10% of the polyorganosiloxane;

c) from about 0.01% to about 10% of a silicone-polyoxyalkylene copolymer surfactant; and d) a carrier comprising:
  (i) at least about 0.5%, by weight of the composition, of a first solvent selected from the group consisting of water; water soluble organic solvents; organic solvents which are strongly to moderately strong in hydrogen-bonding parameter; and mixtures thereof; other than $C_1$–$C_3$ monohydric alcohols, ketones and ethers.

The silicone-polyoxyalkylene copolymer surfactant is selected from silicone-linear polyoxyalkylene copolymers having the formula (I):

$$M'D_bD'_cM' \qquad (I)$$

wherein:

M' is a monofunctional unit $R_2R'SiO_{1/2}$;

D is a difunctional unit $R_2SiO_{2/2}$;

D' is a difunctional unit $RR'SiO_{2/2}$;

R is independently H, $C_1$–$C_6$ alkyl, or aryl;

R' is independently, an oxyalkylene containing moiety, H or $CH_3$;

b is an integer of from about 10 to about 1000; preferably about 10 to about 500, more preferably about 20 to about 200; and c is an integer of from 0 to about 100, provided that when c is 0, at least one M' contains an oxyalkylene moiety; and silicone-graft polyoxyalkylene copolymers having the formula (II):

$MD_bD'_cM$ (II)

wherein
- M is a monofunctional unit $R_3SiO_{1/2}$;
- D is a difunctional unit $R_2SiO_{2/2}$;
- D' is a difunctional unit $RR'SiO_{2/2}$;
- R is independently H, $C_1$–$C_6$ alkyl, or aryl;
- R' is an oxyalkylene containing moiety;
- b is an integer of from about 10 to about 1000; and
- c is an integer of from 1 to about 100.

In a preferred embodiment, the composition further comprises a second solvent selected from $C_1$–$C_3$ monohydric alcohols, $C_1$–$C_3$ ketones, $C_1$–$C_3$ ethers, and mixtures thereof, preferably a $C_1$–$C_3$ monohydric alcohol. Compositions of this type preferably comprise water as the first solvent.

DETAILED DESCRIPTION OF THE INVENTION

The essential components of the present invention are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molecular weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including all patents, patent applications, and printed publications, are hereby incorporated by reference in their entirety in this disclosure.

The term "suitable for application to human hair" as used herein, means that the compositions or components thereof so described are suitable for use in contact with human hair and the scalp and skin without undue toxicity, incompatibility, instability, allergic response, and the like.

The components of the compositions hereof are selected such that the total composition will be compatible. As used herein, compatible means there is no marked phase separation, e.g., excessive cloudiness, layering or precipitation of the composition which negatively impacts the esthetic or functional properties of the composition in a significant manner.

Preferred compositions are those wherein the mixture of essential components, namely the hair styling polymer, silicone emulsion, silicone polyether surfactant and carrier is a substantially homogeneous solution or dispersion (preferably a microdispersion), more preferably substantially clear to translucent in appearance. Preferred final compositions are those also characterized by these properties.

Preferred compositions are those wherein the mixture of essential components provides a % transmittance of at least about 50% at a wavelength of 460 nm as determined by standard spectroscopy methods. Preferred final compositions are those also characterized by these properties.

Hair Styling Polymers

The composition of the present invention comprises a hair styling polymer for providing stylability to the hair. Hair styling polymers possess adhesive properties such that they are capable of shaping or styling the hair, and should be removable by shampooing or rinsing the hair. One or more hair styling polymers may be used. The total amount of hair styling polymer is generally from about 0.01% to about 20%, preferably from about 0.1% to about 15%, more preferably from about 0.5% to about 10%. A variety of hair styling polymers are suitable in the present invention. Particular polymers will be selected by the skilled artisan considering the solubility of the polymer in the composition and the ionicity of the composition.

Suitable hair styling polymers are those which are soluble or dispersible (preferably microdispersible) in the carrier described herein in the weight ratios employed in the composition. Solubility/dispersibility is determined at ambient conditions of temperature and pressure (25° C., 101.3 kPa (1 Atm)). Solubility of the polymer should be determined after neutralization, if any.

Exemplary hair styling polymers include the following:
a) Silicone-Containing Hair Styling Copolymers Suitable hair styling polymers include graft and block copolymers of silicone with a nonsilicone adhesive polymer. Whether graft or block, these copolymers should satisfy the following four criteria:

(1) when dried the copolymer phase-separates into a discontinuous phase which includes the silicone portion and a continuous phase which includes the non-silicone portion;

(2) the silicone portion is covalently attached to the non-silicone portion;

(3) the molecular weight of the silicone portion is from about 1,000 to about 50,000; and (4) the non-silicone portion must render the entire copolymer soluble or dispersible in the hair care composition vehicle and permit the copolymer to deposit on/adhere to hair.

As used herein, phase separation is as described in U.S. Pat. No. 5,658,557, Bolich et al., issued Aug. 19, 1997, hereby incorporated by reference.

The composition preferably contains from about 0.01% to about 20%, more preferably from about 0.1% to about 15%, and most preferably from about 1% to about 10% of the silicone containing hair styling polymer.

Suitable silicone copolymers include the following:
(i) Silicone Graft Copolymers Preferred silicone polymers are the silicone graft copolymers described, along with methods of making them, in U.S. Pat. No. 5,658,557, Bolich et al., issued Aug. 19, 1997, U.S. Pat. No. 4,693,935, Mazurek, issued Sep. 15, 1987, and U.S. Pat. No. 4,728,571, Clemens et al., issued Mar. 1, 1988, each incorporated herein by reference. These silicone-containing copolymers, provide hair conditioning and hair setting characteristics to the composition.

These polymers include copolymers having a molecular weight of from about 10,000 to about 1,000,000, which have a vinyl polymeric backbone having grafted to it monovalent siloxane polymeric moieties, the copolymer comprising C monomers and components selected from the group consisting of A monomers, B monomers, and mixtures thereof. A is at least one free radically polymerizable vinyl monomer, and the amount by weight of A monomer, when used, is up to about 98% of the total weight of all monomers in the copolymer. B is at least one reinforcing monomer copolymerizable with A, and the amount by weight of B monomer, when used, is up to about 98% of the total weight of all monomers in the copolymer. The B monomer is selected from the group consisting of polar monomers and macromers, preferably having a Tg or a $T_m$ above about −20° C. C comprises from about 0.01% to about 50% of the copolymer and is a polymeric monomer having a molecular weight of from about 1,000 to about 50,000 and the general formula

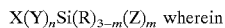

$X(Y)_n Si(R)_{3-m}(Z)_m$ wherein

X is a vinyl group copolymerizabe with the A and B monomers

Y is a divalent linking group

R is a hydrogen, lower alkyl (preferably $C_1$–$C_5$, more preferably $C_1$–$C_3$), aryl or alkoxy Z is a monovalent siloxane polymeric moiety having a number average molecular weight of at least about 500, is essentially unreactive under copolymerization conditions, and is pendant from the vinyl polymeric backbone after copolymerization n is 0 or 1, and m is an integer from 1 to 3.

In another embodiment, the silicone-containing copolymer has a vinyl polymeric backbone, preferably having a $T_g$ above about −20° C., and grafted to the backbone a polydimethylsiloxane macromer having a weight average molecular weight between about 1,000 and about 50,000, preferably from about 5,000 to about 40,000, most preferably about 20,000, wherein the polymer is selected for a given composition such that, when dried, the polymer phase separates into a discontinuous phase which includes the polydimethylsiloxane macromer and a continuous phase which includes the backbone.

The polymers should have a weight average molecular weight of from about 10,000 to about 1,000,000 (preferably from about 30,000 to about 300,000) and, preferably, have a $T_g$ of at least about 20° C. As used herein in reference to these polymers, the abbreviation "$T_g$" refers to the glass transition temperature of the non-silicone backbone, and the abbreviation "$T_m$" refers to the crystalline melting point of the non-silicone backbone, if such a transition exists for a given polymer.

Representative examples of A (hydrophobic) monomers are acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof Preferred A monomers include n-butyl methacrylate, isobutyl methacrylate, t-butyl acrylate, t-butyl methacrylate, 2-ethylhexyl methacrylate, methyl methacrylate, and mixtures thereof.

Representative examples of B monomers (hydrophilic) include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization) vinyl caprolactam, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

Preferably, the C monomer has a formula selected from the following group:

(II)

$X-\overset{O}{\underset{\|}{C}}-O-(CH_2)_{\overline{q}}-(O)_{\overline{p}}-Si(R^4)_{3-m}Z_m$ (III)

$X-Si(R^4)_{3-m}Z_m$ (IV)

$X-\langle\bigcirc\rangle-(CH_2)_{\overline{q}}-(O)_{\overline{p}}-Si(R^4)_{3-m}Z_m$ (V)

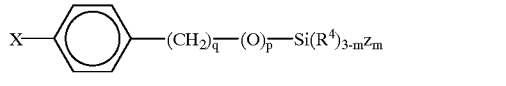

$X-\overset{O}{\underset{\|}{C}}-O-(CH_2)_2-\overset{H}{\underset{|}{N}}-\overset{O}{\underset{\|}{C}}-\overset{R''}{\underset{|}{N}}-\langle\bigcirc\rangle-Si(R^4)_{3-m}Z_m$ (VI)

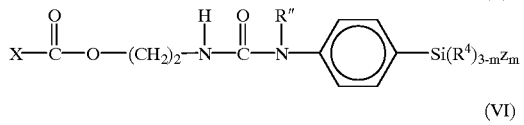

$X-\overset{O}{\underset{\|}{C}}-O-CH_2-\overset{OH}{\underset{|}{CH}}-CH_2-\overset{R''}{\underset{|}{N}}-(CH_2)_{\overline{q}}-Si(R^4)_{3-m}Z_m$ (VII)

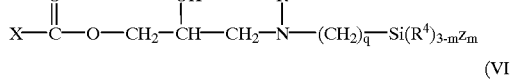

$X-\overset{O}{\underset{\|}{C}}-O-(CH_2)_2-\overset{H}{\underset{|}{N}}-\overset{O}{\underset{\|}{C}}-\overset{R''}{\underset{|}{N}}-(CH_2)_{\overline{q}}-Si(R^4)_{3-m}Z_m$ In those structures, m is 1, 2 or 3 (preferably m=1); p is 0 or 1, preferably 0; R" is alkyl or hydrogen; q in all but (IV) is an integer from 2 to 6, in (IV) q is an integer of from 0 to 6; X is (VIII)

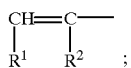

$\begin{array}{c} CH=C-\\ |\quad\ |\\ R^1\ \ R^2 \end{array}$ ;

$R^1$ is hydrogen or —COOH; $R^2$ is hydrogen, methyl or —CH$_2$COOH; Z is (IX)

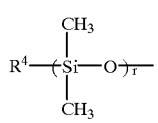

$R^4-(\underset{\underset{CH_3}{|}}{\overset{\overset{CH_3}{|}}{Si}}-O)_{\overline{r}}$ R4 is alkyl, alkoxy, alkylamino, aryl, or hydroxyl (preferably R4 is alkyl); and r is an integer from about 5 to about 700.

The silicone graft polymers generally comprise from 0% to about 98% (preferably from about 5% to about 98%, more preferably from about 20% to about 90%) of monomer A, from about 0% to about 98% (preferably from about 7.5% to about 80%) of monomer B, and from about 0.1% to about 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. In fact, by appropriate selection and combination of particular A, B and C components, the copolymer can be optimized for inclusion in specific vehicles. For example, polymers which are soluble or dispersible in an aqueous formulation preferably have the composition: from about 0% to about 70% (preferably from about 5% to about 70%) monomer A, from about 10% to about 98% (preferably from about 10% to about 80%, more preferably from about 10% to about 60%) monomer B, and from about 1% to about 40% monomer C.

Particularly preferred polymers for use in the present invention include the following (the weight percents below refer to the amount of reactants added in the polymerization reaction, not necessarily the amount in the finished polymer):

acrylic acid/n-butylmethacrylate/(polydimethylsiloxane (PDMS) macromer—20,000 molecular weight) (10/70/20 w/w/w) (polymer molecular weight=80–200M)

N,N-dimethylacrylamide/isobutyl methacrylate/(PDMS macromer—20,000 molecular weight) (20/60/20 w/w/w)(polymer molecular weight=50–300M)

N,N-dimethylacrylamide/(PDMS macromer—20,000 molecular wt) (80/20 w/w)(polymer molecular weight=50–500M)

t-butylacrylate/acrylic acid/(PDMS macromer—12,000–14,000 molecular wt) (60/20/20 w/w/w)(polymer molecular weight=120–150M)

t-butylacrylate/acrylic acid/(PDMS macromer—12,000–14,000 molecular wt) (65/25/10 w/w/w)(polymer molecular weight=100–140M)

t-butylacrylate/acrylic acid/(PDMS macromer—10,000–15,000 molecular wt) (60/20/20 w/w/w)(polymer molecular weight=50–160M)

t-butylacrylate/methacrylic acid/(PDMS macromer—12,000–14,000 molecular wt) (60/20/20 w/w/w)(polymer molecular weight=50–160M)

t-butylacrylate/acrylic acid/(PDMS macromer—2,000–5,000 molecular wt) (60/20/20 w/w/w)(polymer molecular weight=50–150M) quaternized dimethylaminoethyl methacrylate/isobutyl methacrylate/(PDMS macromer—10,000–15,000 molecular wt) (60/20/20 w/w/w)(polymer molecular weight=90–120 M)

(ii) Silicone Block Copolymers

Also useful herein are silicone block copolymers comprising repeating block units of polysiloxanes.

Examples of silicone-containing block copolymers are found in U.S. Pat. No. 5,523,365, to Geck et al., issued Jun. 4, 1996; U.S. Pat. No. 4,689,289, to Crivello, issued Aug. 25, 1987; U.S. Pat. No. 4,584,356, to Crivello, issued Apr. 22, 1986; *Macromolecular Design, Concept & Practice*, Ed: M. K. Mishra, Polymer Frontiers International, Inc., Hopewell Jct., N.Y. (1994), and *Block Copolymers*, A. Noshay and J. E. McGrath, Academic Press, NY (1977), which are all incorporated by reference herein in their entirety. Other silicone block copolymers suitable for use herein are those described, along with methods of making them, in the above referenced and incorporated U.S. Pat. No. 5,658,577.

The silicone-containing block copolymers useful in the present invention can be described by the formulas A-B, A-B-A, and —(A-B)$_n$— wherein n is an integer of 2 or greater. A-B represents a diblock structure, A-B-A represents a triblock structure, and —(A—B)$_n$— represents a multiblock structure. The block copolymers can comprise mixtures of diblocks, triblocks, and higher multiblock combinations as well as small amounts of homopolymers.

The silicone block portion, B, can be represented by the following polymeric structure

wherein each R is independently selected from the group consisting of hydrogen, hydroxyl, $C_1$–$C_6$ alkyl, $C_1$–$C_6$ alkoxy, $C_2$–$C_6$ alkylamino, styryl, phenyl, $C_1$–$C_6$ alkyl or alkoxy-substituted phenyl, preferably wherein R is methyl. In the preceding formula, m is an integer of about 10 or greater, m is an integer of about 40 or greater, more preferably of about 60 or greater, and most preferably of about 100 or greater.

The nonsilicone block, A, comprises monomers selected from the monomers as described above in reference to the A and B monomers for the silicone grafted copolymers. The block copolymers preferably contain up to about 50% (preferably from about 10% to about 20%) by weight of one or more polydimethyl siloxane blocks and one or more non-silicone blocks (preferably acrylates or vinyls).

(iii) Sulfur-Linked Silicone Containing Copolymers

Also useful herein are sulfur-linked silicone containing copolymers, including block copolymers. As used herein in reference to silicone containing copolymers, the term "sulfur-linked" means that the copolymer contains a sulfur linkage (i.e., —S—), a disulfide linkage (i.e., —S—S—), or a sulfilydryl group (i.e.,—SH).

These sulfur-linked silicone containing copolymers are represented by the following general formula:

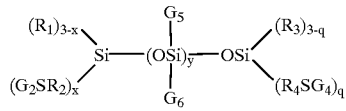

wherein $G_5$ independently represents monovalent moieties which can independently be the same or different selected from the group consisting of alkyl aryl, alkaryl, alkoxy, alkylamino, fluoroalkyl, hydrogen, and —ZSA; A represents a vinyl polymeric segment consisting essentially of polymerized free radically polymerizable monomer, and Z is a divalent linking group. Useful divalent linking groups Z include but are not limited to the following: $C_1$ to $C_{10}$ alkylene, alkarylene, arylene, and alkoxyalkylene. Preferably, Z is selected from the group consisting of methylene and propylene for reasons of commercial availability.

$G_6$ represents monovalent moieties which can independently by the same or different selected from the group consisting of alkyl, aryl, alkaryl, alkoxy, alkylamino, fluoroalkyl, hydrogen, and —ZSA.

$G_2$ comprises A.

$G_4$ comprises A.

$R_1$ represents monovalent moieties which can independently be the same or different and are selected from the group consisting of alkyl, aryl, alkaryl, alkoxy, alkylamino, fluoroalkyl, hydrogen, and hydroxyl. Preferably, $R_1$ represents monovalent moieties which can independently be the same or different selected from the group consisting of $C_{1-4}$ alkyl and hydroxyl for reasons of commercial availability. Most preferably, $R_1$ is methyl.

$R_2$ can independently be the same or different and represents divalent linking groups. Suitable divalent liking groups include but are not limited to the following: $C_1$ to $C_{10}$ alkylene, arylene, alkarylene, and alkoxyalkylene. Preferably, $R_2$ is selected from the group consisting of $C_{1-3}$ alkylene and $C_7$–$C_{10}$ alkarylene due to ease of synthesis of the compound. Most preferably, $R_2$ is selected from the group consisting of —$CH_2$—, 1,3-propylene, and

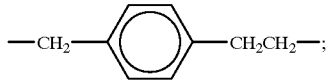

$R_3$ represents monovalent moieties which can independently be the same or different and are selected from the group consisting of alkyl, aryl, alkaryl, alkoxy, alkylamino, fluoroalkyl, hydrogen, and hydroxyl. Preferably, $R_3$ represents monovalent moieties which can independently be the same or different selected from the group consisting of $C_{1-4}$ alkyl and hydroxyl for reasons of commercial availability. Most preferably, $R_3$ is methyl.

$R_4$ can independently be the same or different and represents divalent linking groups. Suitable divalent linking groups include but are not limited to the following: $C_1$ to $C_{10}$ alkylene, arylene, alkarylene, and alkoxyalkylene. Preferably, $R_4$ is selected from the group consisting of $C_{1-3}$ alkylene and $C_7$–$C_{10}$ alkarylene for ease of synthesis. Most preferably, $R_4$ is selected from the group consisting of —$CH_2$—, 1,3-propylene, and

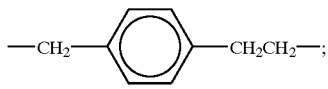

x is an integer of 0–3;
y is an integer of 5 or greater; preferably y is an integer ranging from about 14 to about 700, preferably from about 20 to about 200;
q is an integer of 0–3;
wherein at least one of the following is true:
q is an integer of at least 1;
x is an integer of at least 1;
$G_5$ comprises at least one —ZSA moiety;
$G_6$ comprises at least one —ZSA moiety.

As noted above, A is a vinyl polymeric segment formed from polymerized free radically polymerizable monomers. The selection of A is typically based upon the intended uses of the composition, and the properties the copolymer must possess in order to accomplish its intended purpose. If A comprises a block in the case of block copolymers, a polymer having AB and ABA architecture will be obtained depending upon whether a mercapto functional group —SH is attached to one or both terminal silicon atoms of the mercapto functional silicone compounds, respectively. The weight ratio of vinyl polymer block or segment, to silicone segment of the copolymer can vary. The preferred copolymers are those wherein the weight ratio of vinyl polymer segment to silicone segment ranges from about 98:2 to 50:50, in order that the copolymer possesses properties inherent to each of the different polymeric segments while retaining the overall polymer's solubility.

Sulfur linked silicone copolymers are described in more detail in U.S. Pat. No. 5,468,477, to Kumar et al., issued Nov. 21, 1995, and PCT Application No. WO 95/03776, assigned to 3M, published Feb. 9, 1995, which are incorporated by reference herein in their entirety.

b) Non-Silicone-Containing Hair Styling Polymers

The compositions of the present invention may alternatively or additionally comprise a non-silicone-containing hair styling polymer. Non-silicone-containing hair styling polymers include nonionic, anionic, cationic, and amphoteric polymers, and mixtures thereof. When used, the non-silicone-containing hair styling polymers are preferably present in a combined amount of from about 0.01% to about 20%, more preferably from about 0.1% to about 15%, and most preferably from about 0.5% to about 10% by weight of composition.

Suitable cationic polymers include Polyquaternium-4 (Celquat H-100; L200—supplier National Starch); Polyquaternium-10 (Celquat SC-240C; SC-230 M—supplier National Starch); (UCARE polymer series—JR-125, JR-400, LR-400, LR-30M, LK, supplier Amerchol); Polyquaternium-11 (Gafquat 734; 755N—supplier ISP); Polyquaternium-16 (Luviquat FC 370; FC550; FC905; HM-552 supplier by BASF); PVP/Dimethylaminoethylmethacrylate (Copolymer 845; 937; 958—ISP supplier); Vinyl Caprolactam/PVP/Dimethylaminoethyl Methacrylate copolymer (Gaffix VC-713; H2OLD EP-1—supplier ISP); Chitosan (Kytamer L; Kytamer PC—supplier Amerchol); Polyquaternium-7 (Merquat 550—supplier Calgon); Polyquaternium-18 (Mirapol AZ-1 supplied by Rhone-Poulenc); Polyquaternium-24 (Quatrisoft Polymer LM-200—supplier Amerchol); Polyquaternium-28 (Gafquat HS-100—supplier ISP); Polyquaternium-46 (Luviquat Hold—supplier BASF); and Chitosan Glycolate (Hydagen CMF; CMFP—supplier Henkel); Hydroxyethyl Cetyldimonium Phosphate (Luviquat Mono CP—supplier BASF); and Guar Hydroxylpropyl Trimonium Chloride (Jaguar C series -13S, -14S, -17, 162,-2000, Hi-CARE 1000—supplier Rhône-Poulenc).

Preferred cationic polymers are Polyquaternium-4; Polyquaternium-10; Polyquaternium-11; Polyquaternium-16; PVP/Dimethylaminoethylmethacrylate; Vinyl Caprolactam/PVP/Dimethylaminoethyl Methacrylate copolymer; and Chitosan.

Suitable amphoteric polymers include Octylacrylmide/Acrylates/Butylaminoethyl Methacrylate Copolymer (Amphomer 28-4910, Amphomer LV-71 28-4971, Lovocryl-47 28-4947—National Starch supplier), and Methacryloyl ethyl betaine/methacrylates copolymer (Diaformer series supplier Mitsubishi). Preferred are Octylacrylmide/Acrylates/Butylaminoethyl Methacrylate Copolymer.

Especially preferred polymers for relatively low alcohol systems, e.g., less than about 55% alcohol, are those which are partially zwitterionic in that they always possess a positive charge over a broad range of pH but contain acidic groups which are only negatively charged at basic pH. Therefore the polymer is positively charged at lower pH and neutral (have both negative and positive charge) at higher pHs. The zwitterionic polymer may be selected from cellulose derivatives, wheat derivatives and chitin derivatives such as are known in the art. Nonlimiting examples of zwitterionic polymers useful herein include Polyquaternium-47 (Merquat 2001—supplier Calgon (a zwitterionic copolymer of acrylic acid, methacryl amido propyl trimethyl ammonium chloride, and methyl acrylate)); Carboxyl Butyl Chitosan (Chitolam NB/101—marketed by Pilot Chemical Company, developed by Lamberti); and Dicarboxyethyl Chitosan (N-[(3'-hydroxy-2',3'-dicarboxy)

ethyl]-beta-D-(1,4)-glucosamine) (available from Amerchol as, e.g., CHITOLAN NB/101).

Useful nonionic polymers include PVP or Polyvinylpyrrolidone (PVP K-15, K-30, K-60, K-90, K-120—supplier ISP) (Luviskol K series 12, 17, 30, 60, 80, & 90—supplier BASF); PVP/VA (PVP/VA series S-630; 735, 635, 535, 335, 235—supplier ISP )(Luviskol VA); PVP/DMAPA acrylates copolymer (Styleze CC-10—supplier ISP); PVP/VA/Vinyl Propionate copolymer (Luviskol VAP 343 E, VAP 343 I, VAP 343 PM—supplier BASF); Hydroxylethyl Cellulose (Cellosize HEC—supplier Amerchol); and Hydroxylpropyl Guar Gum (Jaguar HP series -8, -60, -105, -120—supplier Rhone-Poulenc).

Preferred nonionic polymers are PVP or Polyvinylpyrrolidone; PVP/VA; PVP/DMAPA acrylates copolymer; and Hydroxylpropyl Guar Gum.

Anionic polymers suitable for use herein include VA/Crotonates/Vinyl Neodecanonate Copolymer (Resyn 28-2930—National Starch supplier); Butyl Ester of PVM/MA (Gantrez A-425; ES-425; ES-435—supplier ISP); Ethyl Ester of PVM/MA (Gantrez ES-225; SP-215—supplier ISP); Acrylates/acrylamide copolymer (Luvimer 100P; Lumiver Low VOC, supplier BASF); Methacrylate Copolymer (Balance 0/55—National Starch supplier); Vinyl Acetate/Crotonic Acid copolymer (Luviset CA 66—supplier BASF); Isopropyl Ester of PVM/MA Copolymer (Gantrez ES-335—supplier ISP); Acrylates Copolymer; Methacrylates/acrylates copolymer/amine salt (Diahold polymers— supplier Mitsubishi); 2-Butenedioic Acid (Z)—, Monoethyl Ester, Polymer with Methoxyethene (Omnirez 2000); VA/Butyl maleate/Isobornyl Acrylate (Advantage Plus terpolymer—supplier ISP); Acrylates Copolymer (Amerhold DR-25—supplier Amerchol); Acrylates/Hydroxyesteracrylates Copolymer (Acudyne 255 supplier Rohm & Haas); vinyl Acetate/Crotonic Acid/Vinyl Propionate copolymer (Luviset CAP—supplier BASF); PVP/Acrylates copolymer (Luviflex VBM 35—supplier BASF); Diglycol/CHDM/Isophthalates/SIP Copolymer (Eastman AQ 48, AQ 55—supplier Eastman Chemicals); Acrylates/Octacrylamide Copolymer (Versatyl-42 or Amphomer HC—National Starch supplier); TBA/AA copolymer (75/25—Mitsubishi Chemical Corp.); Acrylates Copolymer (Aculyn 33—supplier Rohm & Haas); Acrylates/Steareth-20 Methacrylate Copolymer (Aculyn 22—supplier Rohm & Haas) and Carbomer (supplier B.F. Goodrich).

Preferred anionic polymers are VA/Crotonates/Vinyl Neodecanonate Copolymer; Butyl Ester of PVM/MA; Ethyl Ester of PVM/MA; Acrylates/acrylamide copolymer; Methacrylate Copolymer; and Vinyl Acetate/Crotonic Acid copolymer.

Organopolysiloxane Emulsions

Preferred compositions of the present invention also contain an organopolysiloxane emulsion comprising polysiloxane particles dispersed in a suitable carrier, generally with the aid of a surfactant. The organopolysiloxane emulsion is generally an aqueous emulsion or microemulsion of an organopolysiloxane stabilized in the emulsion or microemulsion by one or more ionic or nonionic surfactants. Such emulsions and microemulsions can be prepared mechanically or by emulsion polymerization. Emulsions and microemulsions used in the present invention are preferably those prepared by emulsion polymerization.

The emulsion is preferably included in an amount such that the composition contains from about 0.01 to about 10% of the dispersed polysiloxane, more preferably about 0.05% to about 6%, most preferably about 0.1% to about 4%. Typically, the composition will include about 0.02 to about 50% of the emulsion.

Organopolysiloxane emulsions can be classified according to the average particle size, or diameter, of the dispersed organopolysiloxane in the emulsion. Emulsions prepared by emulsion polymerization generally comprise an organopolysiloxane as dispersed particles having a diameter of less than about 140 nanometers, more generally less than about 50 nanometers (often referred to as "microemulsions"). Fine emulsions are generally those containing particles of organopolysiloxane with a diameter of about 140–300 nanometers, while standard emulsions are generally those containing organosiloxane particles with a diameter greater than about 300 nanometers. Particle size of an emulsion can be determined by conventional methods, e.g., using a Leeds & Northrup Microtrac UPA particle sizer.

The average particle size of the emulsion used in the present invention is preferably less than about 150 nanometers, more preferably less than about 100 nanometers, even more preferably less than about 80 nanometers, still more preferably less than about 60 nanometers, most preferably less than about 40 nanometers. Silicone emulsions having these particle sizes tend to be more stable and have better external appearance than those having larger particle sizes.

The organopolysiloxane in the emulsion can be a linear or branched chain siloxane fluid having a viscosity of about 20–3,000,000 mm²/s (cs), preferably 300–300,000 cs, more preferably 350–200,000 cs, at 25° C.

Suitable organopolysiloxanes preferably contain the difunctional repeating "D" unit:

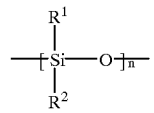

wherein n is greater than 1 and $R^1$ and $R^2$ are each independently $C_1$–$C_7$ alkyl or phenyl. A mixture of siloxanes may be used. Exemplary siloxanes include polydimethylsiloxane, polydiethylsiloxane, polymethylethylsiloxane, polymethylphenylsiloxane, and polydiphenylsiloxane. Siloxane polymers with dimethylsiloxane "D" units are preferred from an economic standpoint. However, $R^1$ and $R^2$ may independently be a functional group other than methyl, e.g., aminoalkyl, carboxyalkyl, haloalkyl, acrylate, acryloxy, acrylamide, mercaptoalkyl or vinyl.

The siloxane may be terminated with hydroxy groups, alkoxy groups such as methoxy, ethoxy, and propoxy, or trimethylsiloxy groups, preferably hydroxy or trimethylsiloxy.

The organopolysiloxane emulsions used herein can be produced by the emulsion polymerization of organosiloxane having a low degree of polymerization in a solvent comprising water. The organopolysiloxane is stabilized in the emulsion by a surfactant, e.g., a nonionic surfactant and an ionic surfactant. The degree of polymerization (DP) of the polysiloxane after emulsion polymerization is preferably in the range of from 3 to 5,000, more preferably in the range of from 10 to 3,000.

The emulsion can be prepared by the emulsion polymerization process described in EP 459500 (published Dec. 4, 1992), incorporated herein by reference. In that process, stable, oil free polysiloxane emulsions and microemulsions are prepared by mixing a cyclic siloxane, a nonionic surfactant, an ionic surfactant, water, and a condensation polymerization catalyst. The mixture is heated and agitated at polymerization reaction temperature until essentially all of the cyclic siloxane is reacted, and a stable, oil free emulsion or microemulsion is formed. The reaction mix, especially surfactant levels, and conditions are controlled in order to provide the desired organopolysiloxane particle size. The emulsions and microemulsions typically have a pH of about 3 to about 10 (e.g., 6–7.5), and contain about 10 to about 70% by weight siloxane polymer, preferably about 20 to about 60%, about 0% to about 30% by weight nonionic surfactant, about 0 to about 30% by weight ionic surfactant, preferably about 0 to about 20%, the balance being water. Preferred emulsions and methods of making them are further described in U.S. patent application Ser. No. 08/929,721, filed on Sep. 15, 1997 in the names of Ronald P. Gee and Judith M. Vincent, incorporated herein by reference in its entirety.

Emulsions can also be produced by the emulsion polymerization process described in EPA 0268982, published Jun. 6, 1988, assigned to Toray, incorporated herein by reference in its entirety. In this process, the emulsion is prepared by a process in which a crude emulsion, consisting of polysiloxane having a low degree of polymerization, a first surfactant (anionic, cationic, and nonionic surfactants), and water, is slowly dripped into an aqueous solution containing a catalytic quantity of a polymerization catalyst and a second surfactant which acts as an emulsifying agent (which may be the same as the first surfactant, however, the surfactants should be compatible in the reaction mixture considering the ionicity of the reaction mixture). The reaction mix and conditions are controlled to provide the desired organopolysiloxane particle size. Therefore, a dropwise addition of the crude emulsion into the aqueous solution of catalyst and surfactant of 30 minutes or longer is preferred in order to produce emulsions having smaller particle sizes. In addition, the quantity of surfactant used in the catalyst plus the surfactant aqueous solution is from about 5 to about 70 weight %, more preferably from about 25 to about 60 per 100 weight parts polysiloxane in the crude emulsion.

Any conventional nonionic surfactant can be used to prepare the emulsion. Exemplary types of nonionic surfactants include silicone polyethers, both grafted and linear block, ethoxylated fatty alcohols, ethoxylated alcohols, ethoxylated alkyl phenols, Isolaureth-6 (polyethylene glycol ether of branched chain aliphatic $C_{12}$ containing alcohols having the formula $C_{12}H_{25}(OCH_2CH_2)_6OH$), fatty acid alkanolamides, amine oxides, sorbitan derivatives (e.g., commercially available from ICI Americas, Inc., Wilmington, Del., under the tradenames SPAN and TWEEN), and propylene oxide-ethylene oxide block polymers (e.g., commercially available from BASF Corp., Parsippany, N.J. under the trademark PLURONIC). Ionic surfactants useful in preparing the emulsion include any conventional anionic surfactant such as sulfonic acids and their salt derivatives. Ionic surfactants also include any conventional cationic surfactant used in emulsion polymerization. Surfactants of these types are well known in the art and are commercially available from a number of sources. Specific examples of these surfactant types are also disclosed in the above referenced patent application Ser. No. 08/929,721.

The surfactant can be used in the form of a single type of surfactant (e.g., anionic, cationic or nonionic), or the surfactant can be used as a combination of two or more types provided that they are compatible with each other and the other components of the composition. Preferred combinations of surfactant types include the combination of two or more types of anionic surfactants, the combination of two or more types of nonionic surfactants, the combination of two or more types of cationic surfactants, the combination of two or more types of surfactants selected from both the anionic and nonionic surfactants; and the combination of two or more types of surfactants selected from both the cationic and nonionic surfactants.

The catalyst employed in the emulsion polymerization may be any catalyst capable of polymerizing cyclic siloxanes in the presence of water, including condensation polymerization catalysts capable of cleaving siloxane bonds. Exemplary catalysts include strong acids and strong bases, ionic surfactants such as dodecylbenzenesulfonic acid, phase transfer catalysts, and ion exchange resins where a catalyst is formed in situ. As will be understood by those skilled in the art, a given surfactant may also serve as the polymerization catalyst (e.g., alkylbenzenesulfonic acids, or quaternary ammonium hydroxides or salt thereof may function as both a surfactant and the polymerization catalyst).

A surfactant system, catalyst and resulting emulsion suitable for use in the compositions of the present invention can be selected by the skilled artisan considering the ionicity of the composition. In general, these materials are selected such that the total composition will be compatible.

Emulsions useful herein also include those produced by a mechanical emulsion process, although those produced by emulsion polymerization are preferred. In mechanical emulsions, the organopolysiloxane is generally present in the emulsion in the form of particles having a diameter greater than about 140 nanometer and less than about 350 nanometer, preferably less than about 300 nanometer. Mechanical emulsions can be prepared by known mechanical processes such as are described in U.S. Pat. No. 5,017,221 (May 21, 1991) and in EP 463431 (Jan. 2, 1992). Typical mechanical emulsions contain a trimethylsiloxy-terminated polydimethylsiloxane stabilized by a nonionic surfactant. According to such mechanical processes, water, one or more nonionic surfactants, and the organopolysiloxane are mixed together, and homogenized using a laboratory homogenizer or other device for applying vigorous agitation. These mechanical emulsions typically have a pH of 7–9.5, and contain 10–80% by weight of the siloxane, preferably 20–60%, 0.01–15% by weight of the nonionic surfactant(s), the balance being water.

Organopolysiloxane emulsions are available from a number of commercial sources. The following organopolysiloxane emulsions are manufactured by Dow Corning of Midland, Mich.

Emulsions containing dimethicone copolyol:

| Emulsion Trade Name | Si Type | Internal phase viscosity (cps) | Surfactant | Si particle, size, nm |
|---|---|---|---|---|
| DC 2-5791 - LP | Dimethylsiloxanol, Dimethyl cyclosiloxane | 70–90M | Triethanolamine dodecylbenzene sulfonate, Polyethylene oxide lauryl ether | 123 |

-continued

| Emulsion Trade Name | Si Type | Internal phase viscosity (cps) | Surfactant | Si particle, size, nm |
| --- | --- | --- | --- | --- |
| DC 2-5791 - MP | Dimethylsiloxanol, Dimethyl cyclosiloxane | 70–90M | Triethanolamine dodecylbenzene sulfonate, Polyethylene oxide lauryl ether | 93 |
| DC 2-5791 | Dimethylsiloxanol, Dimethyl cyclosiloxane | 70–90M | Triethanolamine dodecylbenzene sulfonate, Polyethylene oxide lauryl ether | <50 |
| DC 2-5791 - sp | Dimethylsiloxanol, Dimethyl cyclosiloxane | 70–90M | Triethanolamine dodecylbenzene sulfonate, Polyethylene oxide lauryl ether | <40 |
| DC 2-5932 | Dimethylsiloxanol, Dimethyl cyclosiloxane | 1–2M | Cetrimonium Chloride, Trideceth-12 | <30 |

Emulsions not containing dimethicone copolyol:

| Emulsion Trade Name | Si Type | Internal phase viscosity (cps) | Surfactant | Si particle, size, nm |
| --- | --- | --- | --- | --- |
| DC 2-1470 - LP | Dimethylsiloxanol, Dimethyl cyclosiloxane | 15–20M | Triethanolamine dodecylbenzene sulfonate, Polyethylene oxide lauryl ether | 124 |
| DC 2-1470 - MP | Dimethylsiloxanol, Dimethyl cyclosiloxane | 4–8M | Triethanolamine dodecylbenzene sulfonate, Polyethylene oxide lauryl ether | 94 |
| DC 2-1716 MEM | Dimethylsiloxanol with methyl silsequioxane, Octamethyl cyclotretrasiloxane | 10–30M | Cetrimonium Chloride, Trideceth-12 | 50–80 |
| DC 2-8937 | Mercapto-siloxane | — | Cetrimonium Chloride, Trideceth-12 | 50–70 |
| DC 2-1470 | Dimethylsiloxanol, Dimethyl cyclosiloxane | 15–20M | Triethanolamine dodecylbenzene sulfonate, Polyethylene oxide lauryl ether | <50 |
| DC 2-1845 | Dimethylsiloxanol, Dimethyl cyclosiloxane | 4–8M | Triethanolamine dodecylbenzene sulfonate, Polyethylene oxide lauryl ether | <40 |
| DC 2-1845 - HV | Dimethylsiloxanol, Dimethyl cyclosiloxane | 60–70M | Triethanolamine dodecylbenzene sulfonate, Polyethylene oxide lauryl ether | <35 |
| DC 2-1550 | Dimethylsiloxanol, Dimethyl cyclosiloxane | 100–600M | Triethanolamine dodecylbenzene sulfonate, Polyethylene oxide lauryl ether | ≦50 |
| DC 2-1281 | Dimethylsiloxanol, Dimethyl cyclosiloxane | 1–2M | Cetrimonium Chloride, Trideceth-12 | <30 |
| DC 2-8194 | Dimethyl, aminomethyl propyl siloxane | 4–6M | Cetrimonium Chloride, Trideceth-12 | ≦30 |

In general, emulsions having the smallest particle size are preferred. Where the hair styling polymer is an anionic acrylate polymer, DC 2-1845, and DC 2-5791 are preferred emulsions. When the hair styling polymer is a cationic polymer comprising nitrogen, the DC-2-8194, DC 2-1281, and DC 2-5932 emulsions are preferred.

The silicone emulsion may contain a silicone polyether copolyol, such as described herein. Alternatively or additionally, the compositions hereof may contain a silicone polyether. If the emulsion is supplied as a material not containing a silicone polyether already present in the emulsion, a silicone polyether may be added prior to making the batch composition hereof. Where the polyether is not dispersible in the silicone emulsion, it is preferably mixed in about an equal portion of water containing from 10–50% $C_1$–$C_3$ monohydric alcohol, preferably ethanol, prior to combination with the silicone emulsion.

This pre-mix is then added to the other ingredients of the composition which have preferably been pre-mixed.

Silicone Polyether Surfactant

Compositions of the present invention contain a silicone polyether suitable for stabilizing the organopolysiloxane emulsion. The silicone polyether comprises a polymeric portion comprising repeating organosiloxane units, and a polymeric portion comprising repeating alkylene oxide units (i.e., a silicone-polyoxyalkylene copolymer). Suitable silicone polyethers are those which are surface active in the carrier employed in the compositions of the invention. As will be understood in the art, the surface activity of the silicone polyether will depend on the molecular weight of the polymeric portion comprising repeating organosiloxane units. This portion should be of sufficiently large molecular weight such that it is insoluble in the carrier, yet not so large that it renders the whole molecule insoluble in the carrier. The silicone polyether is preferably used in an amount of from about 0.02% to about 7%, more preferably about 0.05% to about 5%, of the total composition.

The silicone polyether may be a silicone-linear polyoxyalkylene block copolymer (wherein the polymeric backbone comprises silicone blocks and polyoxyalkylene blocks, optionally having grafts), a silicone-graft polyoxyalkylene copolymer (wherein the polymeric backbone comprises silicone blocks and the polyoxyalkylene blocks are present as grafts rather than in the backbone), or a mixture thereof. Linear polyoxyalkylene block copolymers are preferred.

Preferred silicone linear block polyethers suitable for use herein have the formula (I):

M'D$_b$D'$_c$M' wherein

M' is a monofunctional unit $R_2R'SiO_{1/2}$;

D is a difunctional unit $R_2SiO_{2/2}$;

D' is a difunctional unit $RR'SiO_{2/2}$;

R is independently H, $C_1$–$C_6$ alkyl, or aryl, preferably H or $C_1$–$C_4$ alkyl, more preferably $CH_3$;

R' is independently, an oxyalkylene containing moiety, H, or $CH_3$;

b is an integer of from about 10 to about 1000, preferably about 10 to about 500, more preferably about 20 to about 200; and c is an integer of from 0 to about 100, preferably 0 to about 50, more preferably c is 0, provided that when c is 0, at least one M' contains an oxyalkylene moiety.

Preferred R' in structure (I) are those having the formula:

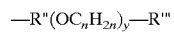

—R"(OC$_n$H$_{2n}$)$_y$—R'"

wherein

R" is a divalent radical for connecting the oxyalkylene portion of moiety R' to the siloxane backbone, preferably —(C$_m$H$_{2m}$)—, wherein m is an integer of from 2 to 8, preferably from 2–6, more preferably from 3–6;

R'" is a terminating radical for the oxyalkylene portion of the moiety R', e.g., H, hydroxyl, $C_1$–$C_6$ alkyl, aryl, alkoxy (e.g., $C_1$–$C_6$) or acyloxy (e.g., $C_1$–$C_6$), preferably hydroxyl;

n is an integer of from 2 to 4, preferably 2 to 3 (i.e., the oxyalkylene group may contain ethylene oxide, propylene oxide and/or butylene oxide units); and y is an integer of 1 or greater, wherein the total y from all the oxyalkylene moieties in the copolymer is about 10 or greater.

The oxyalkylene moiety of R' may be a random copolymer, a block copolymer or a mixture thereof Preferred R' groups in structure (I) are those wherein the oxyalkylene units are selected from ethylene oxide units (EO), propylene oxide units (PO), and mixtures thereof. More preferred are those wherein the oxyalkylene units have an ethylene oxide unit (EO) to propylene oxide unit (PO) ratio of $EO_{10-100}PO_{0-100}$, more preferably $EO_{20-70}PO_{20-70}$, most preferably $EO_{30-70}$ $PO_{30-70}$, based on the total oxyalkylene in the silicone polyether.

Particularly preferred silicone polyethers are those having the formula:

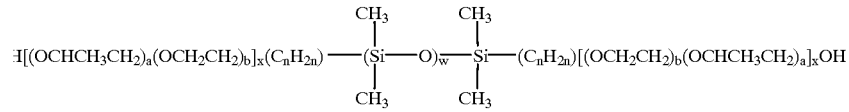

H[(OCHCH$_3$CH$_2$)$_a$(OCH$_2$CH$_2$)$_b$]$_x$(C$_n$H$_{2n}$)—(Si—O)$_w$—Si—(C$_n$H$_{2n}$)[(OCH$_2$CH$_2$)$_b$(OCHCH$_3$CH$_2$)$_a$]$_x$OH with CH$_3$ groups on the Si atoms wherein n is as defined above, x is independently an integer of one or greater; a and b independently are an integer of from about 15 to about 30, and w is an integer of from about 20 to about 200, more preferably from about 30 to about 200.

Such silicone polyethers are commercially available from Goldschmidt Chemical Company under the tradename TEGOPREN 5830.

Preferred silicone graft polyethers for use herein are those having the formula (II):

MD$_b$D'$_c$M wherein:

M is a monofunctional unit $R_3SiO_{1/2}$,

D is a difunctional unit $R_2SiO_{2/2}$,

D' is a difunctional unit $RR'SiO_{2/2}$,

R is independently H, $C_1$–$C_6$ alkyl, or aryl, preferably H or $C_1$–$C_4$ alkyl, more preferably $CH_3$, R' is an oxyalkylene containing moiety, b is an integer of from about 10 to about 1000, preferably about 100 to about 500 c is an integer of from 1 to about 100, preferably 1 to about 50.

Preferred R' are those having the formula

—R"(OC$_n$H$_{2n}$)$_y$—R'"

wherein

R" is a divalent radical for connecting the oxyalkylene portion of moiety R' to the siloxane backbone, preferably —(C$_m$H$_{2m}$)—, wherein m is an integer of from 2 to 8, preferably 2–6, more preferably 3–6;

R'" is a terminating radical for the oxyalkylene portion of moiety R', e.g., H, hydroxyl, C$_1$–C$_6$ alkyl, aryl, alkoxy (e.g., C$_1$–C$_6$) or acyloxy (e.g., C$_1$–C$_6$), preferably hydroxy or acyloxy, more preferably hydroxyl;

n is an integer of from 2 to 4, preferably 2 to 3 (i.e., the oxyalkylene group may contain ethylene oxide, propylene oxide and/or butylene oxide units); and y is 1 or greater.

The oxyalkylene moiety of R' may be a random copolymer, a block copolymer or a mixture thereof. Preferred R' groups are those wherein the oxyalkylene units are selected from ethylene oxide units (EO), propylene oxide units (PO), and mixtures thereof. More preferred are those wherein the oxyalkylene units have an ethylene oxide unit (EO) to propylene oxide unit (PO) ratio of EO$_{10-100}$PO$_{0-100}$, more preferably EO$_{10-30}$PO$_{1-30}$, based on the total oxyalkylene in the silicone polyether.

In this regard, Table 1 shows some representative silicone graft polyethers:

TABLE 1

| Silicone Polyether* | Structure | Weight % EO | Weight % PO | HLB** |
|---|---|---|---|---|
| A | EO | 19 | 0 | 6.8 |
| B | EO | 40 | 0 | 8.0 |
| C | EO/PO | 34 | 0.4 | 6.8 |
| D | EO/PO | 41 | 12 | 8.2 |
| E | EO/PO | 34 | 39 | 5.0 |
| F | EO/PO | 32 | 42 | 6.4 |
| G | EO/PO | 30 | 40 | 5.7 |

*Silicone Polyethers A and B contain less than 20 D units and less than 5 D' units. Silicone Polyethers C–G contain from 100–200 D units and 10–30 D' units.
**Hydrophilic lipophilic balance (HLB) is determined by calculating the weight percent of EO and dividing this value by five.

Silicone polyethers of this type are further described in the above referenced patent application Ser. No. 08/929,721.

Siloxane-oxyalkylene copolymers, i.e., silicone polyethers, can be prepared according to methods generally described in the standard text on silicone chemistry entitled "Chemistry and Technology of Silicones," by Walter Noll, Academic Press Inc., Orlando, Fla., (1968), on pages 373–376. Silicone polyethers are also available from a number of commercial sources such as:

| Trade Name | Supplier | Silicone Content % | EO and/or PO | Molecular Weight |
|---|---|---|---|---|
| D.C.Q2-5220 | Dow Corning[1] | 14 | EO & PO | 3102 |
| D.C.193 | " | 33 | EO | — |
| D.C.190 | " | 24 | EO & PO | 2570 |
| D.C.Q4-3667 | " | 37 | EO | 2400 |
| Silwet L-7200 | OSI[2] | 31 | EO & PO | 19,000 |
| Tegopren 5830/ Abil B8830 | Goldschmidt A.G.[3] | 55 | 40% EO/60% PO | 7800 |
| Tegopren 5830 - A | Goldschmidt A.G.[3] | 50 | 30% EO/70% PO | 9000 |
| Tegopren 5830 - B | Goldschmidt A.G.[3] | 50 | 60% EO/40% PO | 9000 |
| Abil B8851 | Goldschmidt A.G.[3] | — | EO & PO | >1400 |
| Abil B8863 | Goldschmidt A.G.[3] | — | EO & PO | >3000 |
| Abil EM 97 neat | Goldschmidt A.G.[3] | 75 | 60% EO/40% PO | 14,000–15,000 |

[1]Dow Corning of Midland, Michigan
[2]OSI Specialties of Lisle, Il.,
[3]Hopewell, VA Other silicone polyethers are available as SF-1188 offered by General Electric of Waterford, N.Y., and KF353A offered by Shin Etsu Silicones of America of Torrance, Calif.

Additional silicone polyethers are described in U.S. Pat. No. 4,871,529, incorporated herein by reference.

Carrier

The compositions of the invention also comprise a carrier for the essential and optional components. Suitable carriers are those in which the hair styling polymer and silicone polyether surfactant are soluble or dispersible, preferably soluble or microdispersible, and in which the organopolysiloxane is dispersible. Choice of an appropriate carrier will also depend on the particular end use and product form contemplated (e.g., the hair styling polymer to be used, and the product form, e.g., for hair styling compositions such as hair spray, mousse, tonic, lotion or gel). Preferred carriers are those which are suitable for application to the hair, skin, and/or nails, especially the hair.

The carrier is present at from about 0.5% to about 99.5%, preferably from about 5% to about 99.5%, most preferably from about 50% to about 95%, of the composition.

The compositions of the present invention comprise one or more suitable solvents. Preferred solvent systems are those which form a homogeneous solution or dispersion (preferably microdispersion) with the essential components in the weight ratios used in the composition. Preferred solvent systems are those which form a substantially clear to translucent solution or dispersion (preferably microdispersion) with the essential components in the weight ratios used in the composition.

Preferred solvents include those selected from the group consisting of water; water soluble organic solvents; organic solvents which are strongly to moderately strong in hydrogen-bonding parameter; and mixtures thereof; wherein the solvent is other than C$_1$–C$_3$ monohydric alcohol, C$_1$–C$_3$ ketone and C$_1$–C$_3$ ether. Water is a preferred solvent. At least about 0.5%, preferably at least about 1%, of this type of solvent is used in the composition.

Exemplary water soluble organic solvents other than C$_1$–C$_3$ monohydric alcohols, ketones and ethers include propylene glycol, glycerine, phenoxyethanol, dipropylene glycol, sugars, and mixtures thereof.

Solvents which are moderately strong to strong in hydrogen-bonding parameter other than C$_1$–C$_3$ monohydric alcohols, ketones and ethers include esters, ethers, ketones, glycol monoethers (moderately H-bonded) and alcohols, amines, acids, amides and aldehydes (strongly H-bonded). A description and examples of solvents of this type are disclosed in Polymer Handbook, 2d. Ed., J. Brandrup and E. H. Immergut, Editors, John Wiley & Sons, N.Y., 1975, Section IV, page 337–348 (Table 2). Preferred solvents of this type are dibutyl phthalate, propylene carbonate, propylene glycol monomethyl ether, methyl acetate, methyl proprionate and mixtures thereof. Propylene glycol monomethyl ether, methyl acetate, methyl proprionate and mixtures thereof are preferred; methyl acetate is most preferred.

Other solvents suitable for use herein are water soluble, organic volatile solvents selected from $C_1$–$C_3$ monohydric alcohols, $C_1$–$C_3$ ketones, $C_1$–$C_3$ ethers, and mixtures thereof, monohydric alcohols being preferred. Preferred solvents of this type are methylal, ethanol, n-propanol, isopropanol, acetone and mixtures thereof. More preferred are ethanol, n-propanol, isopropanol, and mixtures thereof.

In a preferred embodiment, the carrier comprises (i) a solvent selected from the group consisting of water; water soluble organic solvents; organic solvents which are strongly to moderately strong in hydrogen-bonding parameter; and mixtures thereof; wherein the solvent is other than $C_1$–$C_3$ monohydric alcohol, $C_1$–$C_3$ ketone and $C_1$–$C_3$ ether; (ii) a solvent selected from the groups consisting of $C_1$–$C_3$ monohydric alcohols, $C_1$–$C_3$ ketones, $C_1$–$C_3$ ethers, and mixtures thereof; and (iii) mixtures thereof; preferably a mixture thereof. Especially preferred are a mixture of water and $C_1$–$C_3$ monohydric alcohol, e.g., water-ethanol or water-isopropanol-ethanol. Another particularly preferred solvent system comprises one or more of propylene glycol monomethyl ether, methyl acetate, and methyl proprionate, preferably methyl acetate, optionally with one or more of water or a $C_1$–$C_3$ monohydric alcohol.

The carrier may include other solvents, e.g., hydrocarbons (such as isobutane, hexane, decene, acetone), halogenated hydrocarbons (such as Freon), linalool, volatile silicon derivatives, especially siloxanes (such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof.

Solvents used in admixture may be miscible or immiscible with each other. However, in the final composition such solvents should be compatible with each other and other components in the composition such that solids do not precipitate.

Reduced "volatile organic compound" or "VOC" compositions may be desirable. In this regard, "VOC" refers to those organic compounds that contain less than 12 carbon atoms or have a vapor pressure greater than about 0.1 mm of mercury. For example, the composition may have, as initially applied, a total VOC content of about 95% or less, about 80% or less, about 55% or less (e.g., in preferred hairsprays), about 16% or less (e.g., in preferred mousses), or about 6% or less (e.g., in preferred gels). The VOC may be based on actual VOC content, or the VOC which is delivered upon initial dispensing from a package.

Where the composition comprises a silicone graft hair styling copolymer, the compositions hereof may contain a volatile, nonpolar, branched chain hydrocarbon, which acts as a solvent for the silicone portion of the silicone grafted copolymer. When used, the branched chain hydrocarbon solvent hereof is present at a level of from about 0.01% to about 15%, preferably from about 0.05% to about 10%, more preferably from about 0.1% to about 8%, by weight of the composition.

The branched chain hydrocarbon solvent is characterized by a boiling point of at least about 105° C., preferably at least about 110° C., more preferably at least about 125° C., most preferably at least about 150° C. The boiling point is also generally about 260° C. or less, preferably about 200° C. or less. The hydrocarbon chosen should also be safe for topical application to the hair and skin.

The branched chain hydrocarbon solvents are described in detail in U.S. Pat. No. 5,565,193 and are hereby incorporated by reference. The solvent includes those selected from the group consisting of $C_{10}$–$C_{14}$ branched chain hydrocarbons, and mixtures thereof, preferably $C_{11}$–$C_{13}$ branched chain hydrocarbons, more preferably $C_{12}$ branched chain hydrocarbons. Saturated hydrocarbons are preferred, although it isn't necessarily intended to exclude unsaturated hydrocarbons.

Examples of suitable nonpolar solvents include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). The most preferred nonpolar solvent are $C_{12}$ branched chain hydrocarbons, especially isododecane. Isododecane is commercially available from Preperse, Inc. (South Plainfield, N.J., USA) as Permethyl™ 99A.

The solubility of the silicone portion of the hair styling polymer can be easily determined by verifying whether a silicone polymer of the same composition and molecular weight as that in the hair styling polymer is soluble in the nonpolar hydrocarbon solvent. In general, the silicone polymer should be soluble at 25° C. at a concentration of 0.1% by weight of the hydrocarbon solvent, preferably at 1%, more preferably at 5%, most preferably at 15%.

The nonpolar hydrocarbon solvent, however, is insoluble in the polar solvents of the composition. This is determined in the absence of the hair styling polymer, or other emulsifying agents, and can easily be verified by observing whether the polar and nonpolar solvents form separate phases after being mixed together.

Without intending to be necessarily limited by any particular theory, it is believed that the nonpolar hydrocarbon solvent solubilizes the silicone portion of the hair styling polymer. This is believed to aid in obtaining a smoother, more lubricious polymer film upon drying.

The carrier may also comprise conventional components such as are known in the art suitable for a given product form.

Optional Components

The present compositions can contain a wide variety of other optional ingredients that are suitable for application to human hair, including among them any of the types of ingredients known in the art for use in hair care compositions, especially hair setting compositions like hair spray compositions, mousses, gels and tonics. Generally, such other adjuvants collectively comprise from about 0.05% to about 20% by weight and preferably from about 0.1% to about 10%, by weight of the compositions. Such conventional optional adjuvants are well known to those skilled in the art and include, but are not limited to, plasticizers, surfactants (which may be anionic, cationic, amphoteric or nonionic), neutralizing agents, propellants, hair conditioning agents (e.g., silicone fluids, fatty esters, fatty alcohols, long chain hydrocarbons, isobutene, cationic surfactants, etc.), emollients, lubricants and penetrants such as various lanolin compounds, preservatives, dyes, tints, bleaches, reducing agents and other colorants, sunscreens, vitamins, proteins, thickening agents (e.g., polymeric thickeners, such as xanthan gum) physiologically active compounds for treating the hair or skin (e.g., anti-dandruff actives, hair growth actives), and perfume.

Non-exclusive examples of certain types of optional components are provided below.

a) Plasticizers

The compositions hereof may contain a plasticizer for the hair styling polymer. Any plasticizer suitable for use in hair care products or for topical application to the hair or skin can be used. A wide variety of plasticizers are known in the art. These include glycerine, diisobutyl adipate, butyl stearate, propylene glycol, diethylene glycol, other glycols, tri-$C_2$–$C_8$ alkyl citrates, including triethyl citrate and analogs of triethyl citrate.

Plasticizers are typically used at levels of from about 0.01% to about 200% preferably from about 0.05% to about 100%, more preferably from about 0.1% to about 50% by weight of the polymer.

b) Surfactants

The hair styling compositions can contain one or more surfactants, e.g., for emulsifying hydrophobic components which may be present in the composition. Surfactants are preferred for use in mousse products. Generally, if used such surfactants will be used at a total level of from about 0.01% to about 10%, preferably from about 0.01% to about 5% and more preferably from about 0.01% to about 3%, by weight of the composition. A wide variety of surfactants can be used, including anionic, cationic, amphoteric, and zwitterionic surfactants.

Anionic surfactants include, for example: alkyl and alkenyl sulfates; alkyl and alkenyl ethoxylated sulfates; (preferably having an average degree of ethoxylation of 1 to 10), succinamate surfactants, such as alkylsulfosuccinamates and dialkyl esters of sulfosuccinic acid; neutralized fatty acid esters of isethionic acid; and alkyl and alkenyl sulfonates, including, for example, olefin sulfonates and beta-alkoxy alkane sulfonates. Preferred are allyl and alkenyl sulfates and alkyl and alkenyl ethoxylated sulfates such as the sodium and ammonium salts of $C_{12}$–$C_{18}$ sulfates and ethoxylated sulfates with a degree of ethoxylation of from 1 to about 6, preferably from 1 to about 4, e.g., lauryl sulfate and laureth (3.0) sulfate.

Amphoteric surfactants include those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378. Others include alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof.

Suitable zwitterionic surfactants for use in the present compositions can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

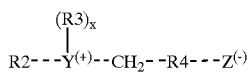

wherein R2 contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; R3 is an alkyl or monohydroxyalkyl group containing 1 to about 3 carbon atoms; x is 1 when Y is sulfur or phosphorus, 1 or 2 when Y is nitrogen; R4 is an alkylene or hydroxyalkylene of from 1 to about 4 carbon atoms and Z is a radical selected from the group consisting of carboxylate, sulfonate, sulfate, phosphonate, and phosphate groups. Classes of zwitterionics include alkyl amino sulfonates, alkyl betaines, and alkyl amido betaines.

Cationic surfactants useful in compositions of the present invention contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

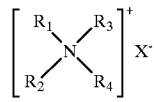

wherein $R_1$ is an aliphatic group of from 1 to 22 carbon atoms, or an aromatic, aryl or alkylaryl group having from 12 to 22 carbon atoms; $R_2$ is an aliphatic group having from 1 to 22 carbon atoms; $R_3$ and $R_4$ are each alkyl groups having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amido groups. Other quaternary ammonium salts useful herein are diquaternary ammonium salts.

Salts of primary, secondary and tertiary fatty amines are also suitable cationic surfactants for use herein. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidyl-behenylamine. Cationic amine surfactants included among those useful in the present invention are disclosed in U.S. Pat. No. 4,275,055, Nachtigal, et al., issued Jun. 23, 1981 (incorporated by reference herein).

Suitable cationic surfactant salts include the halogen, acetate, phosphate, nitrate, citrate, lactate and alkyl sulfate salts.

Nonionic surfactants include polyethylene oxide condensates of alkyl phenols (preferably $C_6$–$C_{12}$ alkyl, with a degree of ethoxylation of about 1 to about 6), condensation products of ethylene oxide with the reaction product of propylene oxide and ethylene diamine, condensation products of aliphatic alcohols with ethylene oxide, long chain (i.e., typically $C_{12}$–$C_{22}$) tertiary amine oxides, long chain tertiary phosphine oxides, dialkyl sulfoxides containing one long chain alkyl or hydroxy alkyl radical and one short chain (preferably $C_1$–$C_3$) radical, silicone copolyols, and $C_1$–$C_4$ alkanol amides of acids having a $C_8$–$C_{22}$ acyl moiety. Preferred nonionic surfactants are $C_1$–$C_4$ alkanol amides of acids having a $C_8$–$C_{22}$ acyl moiety, polyoxyethylene glycol stearyl ethers, and mixtures thereof. Specific examples which are preferred are Lauramide DEA, Steareth-21, Steareth-2, and Na Cocoyl Isethionate.

Additional surfactants suitable for use herein include those described in reference to the emulsion.

c) Neutralizing Agents

Hair styling polymers which have acidic functionalities, such as carboxyl groups, are preferably used in at least partially neutralized form to promote solubility/dispersibility of the polymer. In addition, use of the neutralized form aids in the ability of the dried hair styling compositions to be removed from the hair by shampooing. The degree of neutralization must balance shampoo removability versus humidity resistance. Neutralization levels in excess of what is required for shampoo removability will result in excessively sticky products that will not hold as well in high humidity. When available acidic monomers are neutralized, it is preferred that from about 5% to 60%, more preferably from about 10% to about 40%, and even more preferably from about 12% to about 30% of the polymer (on a total polymer weight basis) be neutralized. The optimal level of neutralization for a specific polymer will depend on the polarity of the monomers selected, the specific ratios of the monomers to each other, and the percentage of acidic monomers. The level of base needed to neutralize the acid groups in a polymer for a specific % neutralization of the polymer may be calculated from the following equation:

$$\% \text{ Base in composition} = A \times (B/100) \times (C/D)$$

A=% Polymer in composition
B=% of polymer to be neutralized (assuming acid groups are available)
C=MW of Base
D=MW of Acid monomer Any conventionally used base, including organic or inorganic (metallic or other) bases, can be used for neutralization of the polymers. Metallic bases are particularly useful in the present compositions. Hydroxides, where the cation is ammonium, an alkali metal or an alkaline earth metal, are suitable neutralizers for use in the present compositions. Preferred inorganic neutralizing agents for use in the compositions of the present invention are potassium hydroxide and sodium hydroxide. For silicone grafted polymers in compositions with water levels>30%, sodium hydroxide is the most preferred inorganic base. Examples of other suitable neutralizing agents which may be included in the hair styling compositions of the present invention include amines, especially amino alcohols such as 2-amino-2-methyl-1,3-propanediol (AMPD), 2-amino-2-ethyl-1,3-propanediol (AEPD), 2-mino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA), dimethyl laurylamine (DML), dimethyl myristalamine (DMM) and dimethyl stearamine (DMS) For silicone grafted polymers, particularly useful amine neutralizing agents are dimethyl myristalamine, dimethyl laurylamine, and mixtures thereof.

Polymers having basic functionalities, e.g., amino groups, are preferably at least partially neutralized with an acid, e.g., hydrochloric acid.

Neutralization can be accomplished by techniques well known in the art, and before or after polymerization of the monomers comprising the hair styling polymer.

d) Hair Conditioning Polymers

The compositions of the invention may include a hair conditioning polymer for purposes of improved wet combing, dry combing and/or improved manageability (e.g., frizz or static control). Hair conditioning polymers are typically used at a level of from about 0.001% to about 6% of the composition, more preferably from about 0.01% to about 4% of the composition.

Cationic and zwitterionic hair conditioning polymers are preferred. Suitable hair conditioning polymers include cationic polymers having a weight average molecular weight of from about 5,000 to about 10 million, and will generally have cationic nitrogen-containing moieties such as quaternary ammonium or cationic amino moieties, and mixtures thereof. Cationic charge density should be at least about 0.1 meq/gram, preferably less than about 3.0 meq/gram, which can be determined according to the well known Kjeldahl Method. Those skilled in the art will recognize that the charge density of amino-containing polymers can vary depending upon pH and the isoelectric point of the amino groups. The charge density should be within the above limits at the pH of intended use. Any anionic counterions can be utilized for the cationic polymers so long as they are compatible.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dictionary*, Sixth Edition, 1995, which is incorporated by reference herein in its entirety.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of poly-vinyl acetate), maleic anhydride, propylene glycol, and ethylene glycol. The cationic polymers are described in detail in U.S. Pat. No. 4,733,677 which is hereby incorporated by reference to further describe the cationic polymers used for conditioning purposes.

The cationic amines can be primary, secondary, or tertiary amines, depending upon the particular species and the pH of the composition. In general, secondary and tertiary amines, especially tertiary amines, are preferred. The cationic polymers can comprise mixtures of monomer units derived from amine- and/or quaternary ammonium-substituted monomer and/or compatible spacer monomers.

Other cationic polymers that can be used include polysaccharide polymers, such as cationic cellulose derivatives, cationic starch derivative, and cationic guar gum derivatives. Other materials include quaternary nitrogen-containing cellulose ethers as described in U.S. Pat. No. 3,962,418, and copolymers of etherified cellulose and starch as described in U.S. Pat. No. 3,958,581, which descriptions are incorporated herein by reference.

Where the composition comprises a neutralized, anionic hair styling polymer and a zwitterionic hair conditioning polymer, the pH of the zwitterion is preferably adjusted to that of the neutralized hair styling polymer prior to combination therewith. Neutralization may be achieved by conventional methods using pH-adjusting agents such as are known in the art.

e) Propellants

When the hair styling compositions are to be dispensed from a pressurized aerosol container (e.g., certain hair sprays and mousses), a propellant which consists of one or more of the conventionally-known aerosol propellants can be used to propel the compositions. A suitable propellant for use can be generally any gas conventionally used for aerosol containers, preferably a liquifiable gas. Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide, and atmospheric gas. For hair sprays and mousses, the selection of appropriate hydrocarbons is made to provide a stable system giving the desired spray/foam quality.

The aerosol propellant may be mixed with the present hair styling compositions and the amount of propellant to be mixed is governed by normal factors well known in the aerosol art. Generally, for liquifiable propellants, the level of propellant is from about 1% to about 60% by weight of the total composition. For hair sprays, the propellant level is from about 10% to about 60% by weight of the total composition, preferably from about 15% to about 50% by weight of the total composition. For mousses, the level of propellant is generally from about 1% to about 30% and more preferably from about 4% to about 15% by weight of the total composition.

Alternatively, pressurized aerosol dispensers can be used where the propellant is separated from contact with the hair styling composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7, 1978, Olofsson and U.S. Pat. No. 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also those previously marketed by The Procter & Gamble Company under their tradename VIDAL SASSOON AIRSPRAY® hair sprays.

Furthermore, non-aerosol foams may also be mixed with the present hair styling composition such that the final composition is dispensable as a stable foam. A composition is "dispensable as a stable foam" when it produces a foam when dispensed from a package or container which is either pressurized or equipped with an air or gas mixing device like the F2 non-aerosol foamer described in U.S. Pat. Nos. 5,271,530; 5,337,929; and 5,443,569; all of which are herein incorporated by reference.

f) Other optional components

Compositions of the invention may contain a variety of other ingredients such as are conventionally used in a given product form. The compositions hereof may be in the form of a hairspray, mousse, gel, lotion, cream, pomade, spray-on product such as spray-on gel, heat protectant spray, volumizing spray, spritz, hair tonic, and the like. The compositions may be aerosol or non-aerosol. Such compositions are described, for example in California Code of Regulations, Regulation for Reducing Volatile Organic Compound Emissions from Consumer Products, Amendment 2, Consumer Products, Sections 94507–94717, Title 17, filed Sep. 19, 1991 and effective Oct. 21, 1991; and in Formulation and Function of Cosmetics, J. S. Jellinek, Wiley-Interscience (1970), each incorporated herein by reference.

Method of Making

The hair styling compositions of the present invention can be made using conventional formulation and mixing techniques. The hair styling polymer and the solvent are mixed to provide a homogeneous mixture. Any other ingredients are then added and mixed to yield the final composition. If the polymer is neutralized, the neutralizer is preferably added prior to addition of other ingredients. For hair spray products, the composition is packaged in conventional mechanical pump spray devices, or alternatively, in the case of aerosol sprays products, the composition is packaged in conventional aerosol canisters along with an appropriate propellant system (also applicable for mousses). Other hair styling compositions including tonics, lotions, and gels, are typically packaged in a conventional bottle or tube.

High water products, containing less than about 50% VOC, such as mousse (16% VOC or less) and gel (6% VOC or less), and containing silicone grafted hair styling copolymer derived from monomers containing acid functional groups are preferably prepared in the following manner. The silicone grafted polymer is dissolved in the compatible, organic solvent, e.g., ethanol or isopropanol, prior to neutralization of the polymer. The solvent used to dissolve the polymer should not contain significant amounts of water and is preferably essentially free of water. If water is added prematurely, either before neutralization or before less than 10% neutralization of the polymer (e.g., neutralization of less than 50% of the acid groups where acid groups are 20% of the polymer structure), then the polymer precipitates as a white insoluble mass. Attempts to complete neutralization after precipitation are generally unsuccessful.

Where water is added after neutralization has occurred, the film quality produced from these modified polymers tends to have a desirable slick and lubricious surface (without intending to be bound by theory, this is usually indicative of silicone present at the surface). Preferred compositions are clear to translucent in appearance. The composition is also stable, preferably retaining within about 10% of its initial clarity with no noticeable precipitate formation for a period of about 6 months or more.

Completion of the neutralization reaction is important for good product clarity, good shampoo removability, and good stability of the composition. However, in compositions having low solvent levels and an effective level of polymer (1–5%), e.g., in typical mousse and gel formulas, the viscosity of the system can increase dramatically with neutralization. This viscosity increase can hinder completion of the neutralization reaction. Therefore, steps should be taken to ensure that the neutralization reaction is complete. For example, this can be ensured by one or more of the following techniques:

1. When the viscosity of the system becomes very thick (typically when about 10% of the polymer has been neutralized), a portion of the water (preferably a minimum 27% of the batch in 6% VOC systems and minimum 10% of the batch in 16% VOC systems) can be added to the system. The water is used in an amount sufficient to lower the viscosity enough in order to achieve good mixing. It is preferred from the standpoint of manufacturing efficiency to add the water portion in one step. However, the water may be added in small increments (e.g., 5% of the batch water), between incremental additions of neutralizer. For example, after the first neutralizer addition (sufficient to neutralize up to about 10% of the polymer) is added with vigorous agitation, then 5% of the batch water can be added, then enough neutralizer to neutralize another 2–4% of the polymer can be added, then another 5% of the batch water addition can be made. This process continues until all the neutralizer is added to the batch. Application of high shear rates to the system, such as can be generated by a Teckmar type milling device, may also be utilized to increase the mass transfer rate, thereby resulting in faster reaction completeness.

2. When a high viscosity has been reached a specially designed high viscosity mixing device, e.g., a dough mixer, may be used. The system is mixed for many hours until reaction completeness can verified analytically (titration, FTIR, or pH), typically up to about 12 hours. A nitrogen blanketed, enclosed system or the like is preferably used to minimize solvent loss during the mix time.

3. Use specialized pressure vessel equipment, heat and agitation. Heat is to be applied while avoiding evaporation of the solvent. Therefore, a nitrogen blanketed pressure vessel should be employed.

The first and third methods above are preferred as being the most efficient. In the absence of the availability of heated pressure vessels (i.e. ambient conditions), the first method is preferred.

In addition, where the composition contains hydrophobic, oily components such as perfume or isoparaffins, steps must be taken to ensure good emulsification of the hydrophobic component in the composition. However, emulsion compositions containing alcohols can be difficult to formulate. Some hydrophobic components such as those mentioned above are relatively difficult to emulsify, typically requiring very high levels of surfactants in order to create reasonably clear systems (which are typically microemulsions). These high levels of surfactants can over plasticize the silicone-grafted polymer, making it unacceptably sticky.

It has been found in the present invention that the hydrophobic components can be readily emulsified by the use of a combination of organic and inorganic neutralizers. Without intending to be limited by theory, it is believed that this combination of neutralizers help the polymer itself to function as an emulsifier by imparting surfactant-like qualities to the polymer. (i.e., a portion of the polymer is relatively hydrophobic and a portion of the polymer is relatively hydrophilic).

The neutralization system comprises a fatty amine neutralizer (preferably selected from dimethyl lauryl amine, dimethyl myristyl amine, amine methyl propanol, dimethylstearyl amine, TEA, and mixtures thereof, more preferably dimethyl lauryl amine, dimethyl myristyl amine and mixtures thereof), in combination with an inorganic neutralizer (preferably metal hydroxides, more preferably NaOH and/or KOH, most preferably NaOH). The amine neutralized acid groups tend to be more hydrophobic than the inorganic neutralized acid groups. Without intending to be bound by theory, it is believed that the amine groups emulsify the hydrophobic components and the inorganic groups provide sufficient water solubility/compatibility and shampoo removability.

When such dual neutralizers are employed, the order of component addition and other process variables become important for preparing the clearest, most stable product. The preferred order of addition and process is as follows: With vigorous agitation:

1. Completely dissolve the polymer in a compatible solvent system containing the water soluble, organic solvent (e.g., ethanol or isopropanol).
2. Add the fatty amine neutralizer in a weight ratio of from 1–6 amine to hydrophobic components to 1–2 amine to hydrophobic components.
3. Add the hydrophobic components.
4. Add any plasticizers.
5. Add the inorganic neutralizer at a level that represents 10%–20% of the polymer (or 50–100% of the available acid groups in a polymer with 20% acrylic acid).
6. When the system becomes very thick (similar to peanut butter), mix the system for at least 10 minutes. Then add water to the mixture in the manner described above, preferably as described for the preferred embodiment of the first method.
7. Mill the system with a high shear mixer such as made by Teckmar for at least 10 minutes.
8. Add the balance of the water and other ingredients required to make the final composition. Gels are preferably dearated, more preferably before the addition of any thickeners.

Whether the hair styling polymer is a silicone graft polymer or other polymer, when the compositions of the present invention comprise a silicone emulsion, it is important to add the silicone emulsions to the system when some water (or other polar material) is present. The water helps to maintain the stability of the silicone emulsions in the composition. The amount of water which is preferably present depends on the type of hair styling polymer and the presence and type of silicone copolyol. Where the composition contains a silicone copolyol having structure (I) (e.g., Tegopren), at least about 0.5% water is preferably present regardless of polymer type. When the composition contains other dimethicone copolyols and the polymer comprises a silicone graft polymer, at least about 10% water is preferably present; where the polymer is other than a silicone graft polymer, at least about 25% water is present.

Additionally, it is desirable to not impart high shear rates to the composition once the silicone emulsion has been added, since shear might break the emulsion. Also, the silicone emulsion is typically added after any thickeners or surfactants.

It is usually desirable to premix the silicone emulsion with a silicone copolyol having structure (I) (e.g., Tegopren) prior to combination with the alcohol.

Method of Use

The compositions of the present invention are used in conventional ways to provide the hair care benefits of the present invention. Such methods generally involve application of an effective amount of the product to dry, slightly damp, or wet hair before and/or after the hair is dried and arranged to a desired style. Application of the product is normally effected by spraying or atomizing the product using an appropriate device, e.g. a mechanical pump spray, a pressurized aerosol container, or other appropriate means. Other hair styling compositions including tonics, lotions, and gels, are typically dispensed from a conventional bottle or tube, and applied directly to the hair or first dispensed to the hand and then to the hair. The composition is then dried or allowed to dry. By "effective amount" is meant an amount sufficient to provide the hair hold and style benefits desired. In general, from about 0.5 g to about 30 g of product is applied to the hair, depending upon the particular product formulation, dispenser type, length of hair, and type of hair style.

The compositions of the present invention can be used in other personal care applications, e.g., in skin care applications, where the benefits of the hair styling polymer (e.g., adhesive/substantive properties) and/or silicone emulsion (e.g., conditioning, softening) would be realized.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example I

The following is a gel composition representative of the present invention:

| Component | Weight % |
|---|---|
| Water | 76.75 |
| Ethanol | 16.00 |
| Polyquaterium - 16[1] | 2.00 |
| Benzophenone - 4[2] | 0.10 |
| Perfume | 0.20 |
| Hydroxylpropyl Guar[3] | 1.00 |
| Silicone Microemulsion (37% active)[4] | 3.00 |
| Preservatives | 0.95 |

[1]Luviquat FC 550, BASF
[2]Uvinul MS-40, BASF
[3]Jaguar HP-105, Rhone-Poulenc
[4]DC-2-5932 silicone microemulsion from Dow Corning with a particle size of 24 nm, a cationic surfactant system, and a silicone with an internal phase viscosity = 1,200 cps.

A premix is prepared by adding the Polyquaternium-16 to 60% of the water under moderate agitation. Next with vigorous agitation, add the Benzophenone, the Ethanol, the Perfume, and the preservatives. The final mix is prepared by adding the hydroxypropyl guar to 30% of the water, mixing vigorously until the guar hydrates completely. Next, add the premix with gentle agitation. Then add the silicone microemulsion (premixed with the remaining water) to the mix with mild agitation.

Example II

The following is a mousse composition representative of the present invention:

Concentrate composition:

| Component | Weight % |
|---|---|
| Ethanol (200 proof) | 10.00 |
| Polyquaternium 11 (20% active)[1] | 12.50 |
| Polyquaternium 4[2] | 0.50 |
| Perfume | 0.10 |
| Water | 72.39 |
| Glycerin | 0.30 |
| Lauramide DEA[3] | 0.20 |
| Steareth 21[4] | 0.10 |
| Silicone Microemulsion (25% active)[5] | 3.00 |
| Preservatives | 0.91 |

[1]Gafquat-755N, ISP
[2]Celquat H-100, National Starch
[3]Monamide 716, Mona
[4]BRIJ 721, ICI
[5]DC-2-5932 silicone microemulsion from Dow Corning with a particle size of 24 nm, a cationic surfactant system, and a silicone with an internal phase viscosity = 1,200 cps.

The first premix is prepared by adding the ethanol to ½ of the water (save remaining ½ for premixing Silicone Microemulsion, preservatives and surfactants). Next, add the Celquat H-100 and mix until uniformly dissolved in ethanol/water. Add the Gafquat-755N and mix until uniformly dissolved. With vigorous agitation, add the perfume and the glycerin.

The second premix is prepared by dissolving the surfactants (Lauramide DEA, Steareth 21) in the remaining water with heat (120° F.) and agitation. Remove the mix from heat when the surfactants are completely dissolved. Next, add the preservatives and the silicone microemulsion to the mix with vigorous agitation.

The final concentrate step involves combining the first and second premixes under vigorous agitation and placing the concentrate in a suitable aluminum can at 7% of total fill with an appropriate mousse valve. The valve is crimped to the can and a vacuum is applied to deaerate. The can is then pressurized with propellant.

| Can Composition: | Weight % |
|---|---|
| Concentrate Composition (above) | 93.00 |
| Hydrofluorocarbon 152A (propellant) | 4.76 |
| Isobutane (A31 propellant) | 2.24 |

Example III

The following is a mousse composition representative of the present invention:

Concentrate composition:

| Component | Weight % |
|---|---|
| Ethanol (200 proof) | 6.00 |
| Butyl Ester of PVM/MA copolymer (50% active)[1] | 4.00 |
| PVP/VA (50% active)[2] | 2.00 |
| Perfume | 0.10 |
| Water | 83.19 |
| Aminomethyl propanol[3] | 0.10 |
| Polyquaterium - 47[4] | 0.30 |
| Lauramide DEA[5] | 0.30 |
| Steareth 21[6] | 0.10 |

-continued

Concentrate composition:

| Component | Weight % |
|---|---|
| Silicone Microemulsion (25% active)[7] | 3.00 |
| Preservatives | 0.91 |

[1]Gantrez ES-425, ISP
[2]PVP/VA 735W, ISP
[3]AMP - regular, Angus
[4]Merquat - 2001, Calgon
[5]Monamide 716, Mona
[6]BRIJ 721, ICI
[7]DC 2-5791 - Silicone microemulsion from Dow Corning with a particle size of 49 nm, an anionic/nonionic surfactant system, and a silicone with an internal phase viscosity = 80,000 cps.

The first premix is prepared by adding the Gantrez and PVP/VA to ethanol. The premix is then neutralized with AMP under vigorous agitation. Under continued agitation, add ½ of the water (save remaining ½ for premixing the Silicone Microemulsion, preservatives and surfactants) and the perfume.

The second premix is prepared by dissolving the surfactants (Lauramide DEA, Steareth 21) in the remaining water with heat (120° F.) and agitation. Remove the mix from heat when the surfactants are completely dissolved. Adjust the pH of the Polyquaterium-47 with AMP to be equal to that of the first neutralized Gantrez premix above. Add the pH adjusted Polyquaterium-47 to the mix with vigorous agitation. Next, add the preservatives and the silicone microemulsion to the mix with vigorous agitation.

The final concentrate step involves combining the first and second premixes under vigorous agitation and placing the concentrate in a suitable aluminum can at 7% of total fill with an appropriate mousse valve. The valve is crimped to the can and a vacuum is applied to deaerate. The can is then pressurized with propellant.

| Can Composition: | Weight % |
|---|---|
| Concentrate Composition (above) | 93.00 |
| Hydrofluorocarbon 152A (propellant) | 4.76 |
| Isobutane (A31 propellant) | 2.24 |

Example IV

The following is a Non-Aerosol Hairspray composition representative of the present invention:

| Component | Weight % |
|---|---|
| Ethanol (200 proof) | 55.00 |
| Acrylate Copolymer[1] | 4.00 |
| Dimethyl myristalamine | 0.10 |
| Isododecane[2] | 0.50 |
| Perfume | 0.10 |
| Diisobutyl Adipate[3] | 0.10 |
| Sodium Hydroxide Solution (30% active) | 1.29 |
| Water | 34.91 |
| Silicone Microemulsion (25% active)[4] | 4.00 |

[1]75/25 Terbutylacrylate/Acrylic Acid/, polymer molecular weight = 80,000
[2]Permethyl 99A, Presperse Inc.
[3]Plasthall DIBA, C. P. Hall
[4]DC-2-5791 - Silicone microemulsion from Dow Corning with a particle size of 49 nm, an anionic/nonionic surfactant system, and a silicone with an internal phase viscosity = 77,000.

This product is prepared by completely dissolving the Acrylate Copolymer in ethanol with vigorous agitation (there should be no visible white flakes). Under continued vigorous agitation, add the dimethyl myristal amine, the Isododecane, and the DIBA. While still agitating, slowly add the NaOH. It is important to achieve a complete neutralization reaction. Next, add the perfume under agitation. Then add the water and mix until a uniform mixture results. Finally, add the silicone microemulsion to the mix with agitation.

Examples V–VII

The following are mousse compositions representative of the present invention:

Concentrate composition:

| Component | V | VI | VII |
|---|---|---|---|
| Ethanol (200 proof) | 8.00 | 14.00 | 10.00 |
| Acrylate Dimethicone Copolymer[1] | 2.00 | 3.50 | 3.0 |
| Dimethyl Laurylamine[2] | 0.18 | 0.16 | 0.16 |
| Isododecane[3] | 0.50 | 0.50 | 0.50 |
| Perfume | 0.10 | 0.10 | 0.10 |
| Sodium Hydroxide Solution (30% active) | 0.56 | 1.07 | 0.92 |
| Water | 81.70 | 74.81 | 80.31 |
| Polyquaternium 47 (20% active)[4] | 2.50 | 2.50 | 1.50 |
| Oleyl Alcohol[5] | 0.10 | — | — |
| Lauramide DEA[6] | 0.20 | 0.20 | 0.40 |
| Steareth 21[7] | 0.10 | 0.10 | 0.20 |
| Steareth 2[8] | 0.15 | 0.15 | — |
| Silicone Microemulsion (25% active)[9] | 3.00 | 2.00 | 2.00 |
| Preservatives | 0.91 | 0.91 | 0.91 |

[1]60/20/20 Tetrbutylacrylate/Acrylic Acid/12K silicone macromer, polymer molecular weight 128,000, e.g., Diahold ME, Mitsubishi Chemical Corp.
[2]C12 Alkyl Dimethyl Amine, AT-1295 LT
[3]Permethyl 99A, Presperse Inc.
[4]Merquat 2001, Calgon
[5]NOVOL, Shinnihon RIKA
[6]Monamide 716, Mona
[7]BRIJ 721, ICI
[8]BRIJ 72, ICI
[9]DC-2-5791- Silicone microemulsion from Dow Corning with a particle size of 37 nm, an anionic/nonionic surfactant system, and a PDMS silicone with an internal phase viscosity = 95,000 cps.

A first premix is prepared as follows. Completely dissolve the Acrylate Dimethicone Copolymer in ethanol with vigorous agitation. Add the Dimethyl Laurylamine, Isododecane and perfume. With vigorous agitation, slowly add the NaOH and mix to achieve a complete neutralization reaction. Next, add half of the water and mill until a uniform, relatively thin mixture results.

Separately, a second premix is prepared as follows. First dissolve the surfactants (Lauramide DEA, Steareth 721, & Steareth 21) in the remaining water with heat (120° F.) and agitation. Next, remove the premix from heat when surfactants are completely dissolved. Adjust the pH of the Polyquaternium-47 with NaOH to be equal to that of the completed first premix (about 7.5–8.0 pH). With vigorous agitation, add the Polyquaternium 47, Oleyl alcohol, preservatives, and then the silicone microemulsion.

Proceed to combine Premix 1 and Premix 2 with vigorous agitation to form a concentrate. Combine the concentrate with suitable propellants and package in a conventional manner. For example, the final composition may contain: Concentrate Composition (93 wt. %); Hydrofluorocarbon 152A (4.76 wt. %); and Isobutane A31 (2.24 wt. %).

Example VIII

The following is a mousse composition representative of the present invention:

| Component | Weight % |
| --- | --- |
| Ethanol (200 proof) | 10.00 |
| Cationic Dimethicone Copolymer[1] | 3.00 |
| Water | 83.24 |
| Perfume | 0.10 |
| Lauramide DEA[2] | 0.40 |
| Steareth 21[3] | 0.20 |
| Steareth 2[4] | 0.15 |
| Silicone Microemulsion (25% active)[5] | 2.00 |
| Preservatives | 0.91 |

[1] 40/40/20 - Dimethyl acrylamide/Trimethyl aminoethylmethacrylate chloride salt/10K Si macromer; MW = 60,000
[2] Monamide 716, Mona
[3] BRIJ 721, ICI
[4] BRIJ 72, ICI
[5] DC-2-5932 silicone microemulsion from Dow Corning with a particle size of 24 nm, a cationic surfactant system, and a silicone with an internal phase viscosity = 1,200 cps.

A first premix is prepared as follows. Completely dissolve the Cationic Dimethicone Copolymer in ethanol with vigorous agitation. Add half of the water and mill until a uniform, relatively thin mixture results.

Separately, a second premix is prepared as follows. Dissolve the surfactants (Lauramide DEA and Steareth 21) in the remaining water with heat (120° F.) and agitation. Remove the premix from heat once the surfactants are completely dissolved. With vigorous agitation, add preservatives and perfume, then the silicone microemulsion.

Combine Premix 1 and Premix 2 with vigorous agitation to form a concentrate. Then, combine the concentrate with suitable propellants and package in a conventional manner. For example, the final composition may contain: Concentrate Composition (93 wt. %); Hydrofluorocarbon 152A (4.76 w. %); and Isobutane A31 (2.24 wt. %).

Examples IX and X

The following is a gel composition representative of the present invention:

| | Weight % | |
| --- | --- | --- |
| Component | IX | X |
| Isopropanol | 7.00 | 4.00 |
| Acrylate Dimethicone Copolymer[1] | 3.50 | 2.00 |
| Dimethyl Myristalamine[2] | 0.23 | 0.13 |
| Isododecane[3] | 0.50 | 0.50 |
| Perfume | 0.10 | 0.10 |
| Diethylene Glycol[4] | 0.35 | 0.35 |
| Sodium Hydroxide Solution (30% active) | 1.04 | 0.56 |
| Water | 82.87 | 87.20 |
| Glycerol Polymethacrylate Mixture[7] | — | 0.25 |
| Glycerine | 0.25 | — |
| Hydroxylpropyl Guar[5] | 1.25 | 1.00 |
| Silicone Microemulsion (25% active)[6] | 2.00 | 3.00 |
| Preservatives | 0.91 | 0.91 |

[1] 60/20/20 Terbutylacrylate/Acrylic Acid/12K silicone macromer, polymer molecular weight 128,000
[2] C12 Alkyl Dimethyl Amine, AT-1295 LT
[3] Permethyl 99A, Presperse Inc.
[4] Diethylene glycol, Ashland
[5] Jaguar HP-105, Rhone-Poulenc
[6] DC-2-5791 (sp) silicone microemulsion from Dow Corning with a particle size of 37 nm, an anionic/nonionic surfactant system, and a silicone with an internal phase viscosity = 95,000.
[7] Lubrajel Oil, distributed by ISP, United-Guardian A first premix is prepared by completely dissolving the Acrylate Dimethicone Copolymer in ethanol with vigorous agitation. Under continuing agitation, add the Dimethyl Myristalamine, Isododecane and perfume, the Diethylene glycol, then slowly add the NaOH and mix to achieve a complete neutralization reaction. Next, add 33% of the batch water (premixed with glycerin or Lubrajel oil, preservatives) and mill until a uniform, relatively thin mixture results.

Separately, a second premix is prepared by dissolving the Hydroxylpropyl guar in 43% of the batch water (100° F.) until the guar is fully hydrated. Add the silicone microemulsion (premixed with the remaining water) to the mix with mild agitation.

Combine Premix 1 and Premix 2 with vigorous agitation to form a concentrate.

Example XI

The following is a gel composition representative of the present invention:

| Component | Weight % |
| --- | --- |
| Isopropanol | 6.00 |
| Acrylate Dimethicone Copolymer[1] | 3.00 |
| Dimethyl Myristalamine[2] | 0.20 |
| Isododecane[3] | 0.50 |
| Perfume | 0.10 |
| Diisobutyl Adepate[4] | 0.45 |
| Sodium Hydroxide Solution (30% active) | 0.92 |
| Water | 83.59 |
| Acrylates Steareth Itaconate copolymer[5] | 2.00 |
| Sodium Hydroxide Solution (30% active) | 0.33 |
| Silicone Microemulsion (25% active)[6] | 2.00 |
| Preservatives | 0.91 |

[1] 60/20/20 Terbutylacrylate/Acrylic Acid/12K silicone macromer, polymer molecular weight 128,000
[2] C12 Alkyl Dimethyl Amine, AT-1295 LT
[3] Permethyl 99A, Presperse Inc.
[4] Plasthall DIBA, C. P. Hall
[5] Structure 2001, National Starch
[6] DC-2-5791 (sp) silicone microemulsion from Dow Corning with a particle size of 37 nm, an anionic/nonionic surfactant system, and a silicone with an internal phase viscosity = 95,000.

A first premix is prepared by completely dissolving the Acrylate Dimethicone Copolymer in ethanol with vigorous agitation. Under constant agitation, add Dimethyl Myristalamine, isododecane, perfume, and Diethylene glycol. Next, slowly add the NaOH and mix to achieve a complete neutralization reaction. Add 33% of the batch water (premixed with DIBA & preservatives) and mill until a uniform, relatively thin mixture results.

Separately, a second premix is prepared by dissolving the Structure 2001 thickeners in 43% of the batch water with vigorous agitation until fully hydrated. Neutralize with NaOH ($2^{nd}$ addition) with vigorous agitation until viscosity is consistent. Under mild agitation, add the silicone microemulsion (premixed with the remaining water) to the mix.

Combine Premix 1 and Premix 2 with agitation to form a concentrate.

Example XII

The following is a styling lotion composition representative of the present invention:

| Component | Weight % |
| --- | --- |
| Ethanol | 6.00 |
| Acrylate Dimethicone Copolymer[1] | 2.00 |

-continued

| Component | Weight % |
|---|---|
| Dimethyl Myristalamine[2] | 0.30 |
| Isododecane[3] | 1.00 |
| Perfume | 0.10 |
| Diisobutyl Adepate[4] | 0.45 |
| Sodium Hydroxide Solution (30% active) (1st addition) | 0.59 |
| Water | 84.72 |
| Preservatives | 0.91 |
| PVM/MA Decadiene[5] | 1.00 |
| Sodium Hydroxide Solution (30% active) (2nd addition) | 0.93 |
| Silicone Microemulsion (25% active)[6] | 2.00 |

[1] 60/20/20 Terbutylacrylate/Acrylic Acid/12K silicone macromer, polymer molecular weight 128,000
[2] C12 Alkyl Dimethyl Amine, AT-1295 LT
[3] Permethyl 99A, Presperse Inc.
[4] Plasthall DIBA, C. P. Hall
[5] Stabileze QM; ISP
[6] DC-2-5791 silicone microemulsion from Dow Corning with a particle size of 49 nm, an anionic/nonionic surfactant system, and a silicone with an internal phase viscosity = 77,000.

A first premix is prepared by completely dissolving the Acrylate Dimethicone Copolymer in ethanol with vigorous agitation. Add the Dimethyl Myristalamine, the Isododecane and perfume, and then add the Diethylene glycol. Under continued agitation, slowly add the NaOH and mix to achieve a complete neutralization reaction (not all the NaOH is added here—0.59% of the compositon is added). Add 33% of the batch water (premixed with DIBA & preservatives) and mill until a uniform, relatively thin mixture results.

Separately, a second premix is prepared by dissolving the Structure 2001 thickeners in 43% of the batch water with vigorous agitation until fully hydrated. Next, neutralize with NaOH (remaining quantity—0.93% of the composition) with vigorous agitation until the viscosity is consistent. Add the silicone microemulsion (premixed with the remaining water) to the mix with mild agitation.

Combine Premix 1 and Premix 2 with agitation to form a concentrate.

Examples XIII–XVII

The following are Non-Aerosol Hairspray compositions representative of the present invention:

| | Weight % | | | | |
|---|---|---|---|---|---|
| Component | XIII | XIV | XV | XVI | XVII |
| Ethanol (200 proof) | 72.00 | 79.00 | 67.56 | 55.00 | 55.00 |
| Silicone Multiblock Polymer[1] | — | — | — | — | 4.00 |
| Acrylate Dimethicone Copolymer[2] | 4.50 | 3.00 | — | — | — |
| Acrylate Dimethicone Copolymer[3] | — | — | 4.50 | — | — |
| Acrylate Dimethicone Copolymer[4] | — | — | — | 4.00 | — |
| Acrylate Copolymer[5] | — | — | 1.50 | — | — |
| Isododecane[6] | 0.70 | 0.70 | 1.00 | 0.50 | 0.50 |
| Perfume | 0.10 | 0.10 | 0.10 | 0.10 | 0.10 |
| Diisobutyl Adipate[7] | 0.45 | 0.30 | 0.90 | 0.10 | 0.40 |
| Sodium Hydroxide Solution (30% active) | 1.45 | 0.92 | 1.44 | 1.29 | 1.29 |
| Water | 19.30 | 13.98 | 20.00 | 35.01 | 36.71 |
| Silicone Microemulsion (25% active)[8] | 1.50 | — | 3.00 | — | 2.00 |
| Silicone Microemulsion (25% active)[9] | — | 1.43 | — | 4.00 | — |
| Dimethicone Copolyol[10] | — | 0.57 | — | 0.40 | — |

[1] 40/28/10/12/10 Terbutyl acrylate/Acrylic Acid/Methacrylic Acid/Silicone block (VPS-1001)
[2] 64/20/16 Terbutylacrylate/Acrylic Acid/14K silicone macromer, polymer molecular weight = 150,000
[3] 60/20/20 Terbutylacrylate/Acrylic Acid/14K silicone macromer, polymer molecular weight = 80,000
[4] 75/20/5 Terbutylacrylate/Acrylic Acid/14K silicone macromer, polymer molecular weight = 100,000
[5] 75/25 Terbutylacrylate/Acrylic Acid, polymer molecular weight = 80,000
[6] Permethyl 99A, Presperse Inc.
[7] Plasthall DIBA, C. P. Hall
[8] DC-2-5791 silicone microemulsion from Dow Corning with a particle size of 49 nm, an anionic/nonionic surfactant system, and a silicone with an internal phase viscosity = 77,000
[9] DC-1845 silicone microemulsion from Dow Corning with a particle size of 25 nm, an anionic/nonionic surfactant system, and a silicone with an internal phase viscosity = 80,000 cps
[10] DC 190, Dow Corning Completely dissolve the Acrylate Dimethicone Copolymer and the Acrylate Copolymer in ethanol with vigorous agitation. With vigorous agitation, add the Isododecane and the DIBA, then slowly add the NaOH and mix to achieve a complete neutralization reaction. Add 90% of the water and mix until a uniform mixture results. With agitation, add the perfume and then the silicone microemulsion (premixed with the remaining water and DC 190, if applicable).

Examples XVIII and XIX

The following Aerosol Hairspray compositions are representative of the present invention:

| | Weight % | |
|---|---|---|
| Component | XVIII | XIX |
| Ethanol (200 proof) | 54.67 | 26.50 |
| Acrylate Dimethicone Copolymer[1] | 2.00 | — |
| Acrylate Dimethicone Copolymer[2] | — | 3.50 |
| Isododecane[3] | 0.50 | 0.50 |
| Perfume | 0.10 | 0.10 |
| Diisobutyl Adipate[4] | 0.20 | 0.20 |
| Potassium Hydroxide Solution (45% active) | 0.55 | 0.98 |
| Water | 14.80 | 39.04 |
| Silicone Microemulsion (25% active)[5] | 2.00 | 1.00 |
| Corrosion Inhibitors | 0.18 | 0.18 |
| Dimethyl Ether (propellant) | 12.5 | 14.0 |
| Isobutane (propellant) | 12.5 | 14.0 |

[1] 60/20/20 Terbutylacrylate/Acrylic Acid/14K silicone macromer, polymer molecular weight = 130,000
[2] 70/20/10 Terbutylacrylate/Acrylic Acid/14K silicone macromer, polymer molecular weight = 100,000
[3] Permethyl 99A, Presperse Inc.
[4] Plasthall DIBA, C. P. Hall
[5] DC-2-5791 (sp) silicone microemulsion from Dow Corning with a particle size of 37 nm, an anionic/nonionic surfactant system, and a silicone with an internal phase viscosity = 95,000 cps.

A premix is prepared by completely dissolving the Acrylate Dimethicone Copolymer and the Acrylate Copolymer in ethanol with vigorous agitation. Under continued agitation, add the Isododecane and the DIBA, then slowly add the NaOH and mix to achieve a complete neutralization reaction. Next, add 90% of the water and mix until a uniform mixture results. As agitation continues, add the perfume and then the silicone microemulsion premixed with the remaining water).

Concentrate is put into a suitable container, with a suitable valve and is pressurized with the propellants.

The following are hair spray compositions with varying levels of VOC which are representative of the present invention:

Examples XX–XXII

| Component | Weight % | | |
|---|---|---|---|
| Example | XX | XXI | XXII |
| SDA 40 Alcohol | 90.00 | 80.00 | 55.00 |
| Amphomer 28-4910[1] | 4.00 | 4.00 | 4.00 |
| Aminomethylpropanol[2] | 0.72 | 0.72 | 0.72 |
| Distilled Water | 3.08 | 13.08 | 38.08 |
| SiME/Surfactant Premix 1A | 2.20 | 2.20 | 2.20 |
| Total | 100.00 | 100.00 | 100.00 |
| SiME/Surfactant Premix | 1A | | |
| DC-2-1550[3] | 72.73 | | |
| Tegopren 5830[4] | 27.27 | | |
| Total | 100.0 | | |

[1]Commercially available from National Starch
[2]Commercially available from Angus
[3]Si microemulsion available from Dow Corning
[4]Available from Goldschmidt The premix is prepared by mixing the silicone microemulsion and Tegopren at a lowshear mix rate. Note that the material will gel once thoroughly mixed. Set aside for later use.

In order to prepare the max, add Amphomer to alcohol with vigorous agitation to aid in dispersing. Once dissolved, add aminomethylpropanol followed by DRO water with moderate agitation. Add silicone microemulsion premix with moderate agitation and stir for additional ½ hour to allow thorough mixing.

The following are hair spray compositions with different silicone microemulsions and different emulsifying reactants which are representative of the present invention.

Examples XXII–XXVII

| Component | Weight % | | | | |
|---|---|---|---|---|---|
| Example | XXIII | XXIV | XXV | XXVI | XXVII |
| SDA 40 Alcohol | 55.00 | 80.00 | 80.00 | 48.83 | 80.00 |
| Amphomer 28-4910[1] | 4.00 | 4.00 | 4.00 | 3.75 | 4.00 |
| Aminomethylpropanol[2] | 0.72 | 0.72 | 0.72 | 0.82 | 0.72 |
| Distilled Water | 38.08 | 10.48 | 13.08 | 14.00 | 13.08 |
| Dimethyl ether | — | — | — | 20.00 | — |
| Isobutane | — | — | — | 10.00 | — |
| Fragrance | — | 0.20 | — | 0.10 | — |
| Diisobutyl adipate | — | — | — | .30 | — |
| SiME/Surfactant Premix 8A | 2.20 | — | — | — | — |
| SiME/Surfactant Premix 9A | — | 4.60 | — | — | — |
| SiME/Surfactant Premix 10A | — | — | 2.20 | — | — |
| SiME/Surfactant Premix 11A | — | — | — | 2.20 | — |
| SiME/Surfactant Premix 12A | — | — | — | — | 2.20 |
| Total | 100.00 | 100.00 | 100.00 | 100.00 | 100.00 |
| SiME/Surfactant Premix | 8A | 9A | 10A | 11A | 12A |
| DC-2-1550[3] | 72.73 | 86.96 | 72.73 | 65.00 | — |
| DC-2-8676[3] | — | — | — | — | 72.73 |
| Tegopren 5830 A[5] | 27.27 | 13.04 | — | — | — |
| Tegopren 5830 B[5] | — | — | 27.27 | — | — |
| Tegopren 5830 [5] | — | — | — | 35.00 | 27.27 |
| Total | 100.00 | 100.00 | 100.00 | 100.00 | 100.00 |

[1]Commercially available from National Starch
[2]Commercially available from Angus
[3]Si microemulsions available from Dow Corning
[4]Silicone Copolyol Surfactant available from Dow Corning
[5]Available from Goldschmidt The premix is prepared by mixing the silicone microemulsion and silicone copolyol surfactant with low shear mixing. Note that the material will gel once thoroughly mixed. Set aside for later use.

In order to prepare the main mix, add Amphomer to alcohol with vigorous agitation to aid in dispersing. Once dissolved, add plasticizer, neutralizer and DRO water with moderate agitation. Add silicone microemulsion premix with moderate agitation and stir for additional ½ hour to allow thorough mixing. For the aerosol example XXVI, all of the ingredients except for the DME and isobutane are premixed until dissolved. That mix is then put into an aerosol can, valve placed and crimped, and then the propellants are added through the valve.

The following are hair spray compositions with different styling polymers which are representative of the present invention.

| Component | Weight % | | | |
|---|---|---|---|---|
| Example | XXVIII | XXIX | XXX | XXXI |
| SDA 40 Alcohol | 80.00 | 55.00 | 55.00 | 78.63 |
| Amphomer 28-4910[1] | 4.00 | — | — | — |
| Resyn 28-2930[1] | — | 4.00 | — | — |
| PVP/VA[2] | — | — | 4.00 | — |
| Styling Polymer[3] | — | — | — | 4.42 |
| Diisobutyl Adipate[4] | — | — | — | 0.44 |
| 30% NaOH Solution | — | 0.56 | — | 1.41 |
| Aminomethylpropanol[5] | 0.72 | — | — | — |
| Distilled Water | 13.08 | 35.84 | 36.40 | 13.39 |
| SiME/Surfactant Premix 4A | 2.20 | — | — | — |
| SiME/Surfactant Premix 5A | — | 4.60 | — | — |
| SiME/Surfactant Premix 6A | — | — | 4.60 | — |
| SiME/Surfactant Premix 7A | — | — | — | 1.71 |
| Total | 100.00 | 100.00 | 100.00 | 100.00 |
| SiME/Surfactant Premix | 4A | 5A | 6A | 7A |
| DC-2-1550[6] | — | — | 86.96 | — |
| DC-2-5791[6] | — | 86.96 | — | — |
| DC-2-1716[6] | 72.73 | — | — | — |
| DC-2-1845[6] | — | — | — | 73.10 |
| Tegopren 5830[7] | 27.27 | 13.04 | 13.04 | 26.90 |
| Total | 100.00 | 100.00 | 100.00 | 100.00 |

[1]Commercially available from National Starch
[2]Commercially available from BASF AG
[3]poly[acrylic acid-co-methacrylic acid-co-tert-butyl acrylate-co-n-butyl acrylate]-graft-poly[dimethylsiloxane], wt % composition - AA/MAA/tBA/nBA/SMM - 12/10/36/27/15, MW = 201,000
[4]Commercially available from Croda
[5]Commercially available from Angus
[6]Si microemulsions available from Dow Corning
[7]Available from Goldschmidt The premix is prepared by mixing the silicone microemulsion and silicone copolyol surfactant with low shear mixing. Note that the material will gel once thoroughly mixed. Set aside for later use.

In order to prepare the main mix, add Amphomer to alcohol with vigorous agitation to aid in dispersing. Once dissolved, add plasticizer, neutralizer and DRO water with moderate agitation. Add silicone microemulsion premix with moderate agitation and stir for additional ½ hour to allow thorough mixing.

What is claimed is:

1. A personal care composition suitable for styling hair comprising:
   a) from about 0.01% to about 20% of a hair styling polymer;
   b) a polyorganosiloxane emulsion comprising:
      (i) a polyorganosiloxane dispersed as particles in the emulsion, the polyorganosiloxane having an average particle size of less than about 150 nanometers, and
      (ii) a surfactant system for dispersing the organopolysiloxane in the emulsion,; wherein the amount of emulsion is such that the personal care composition comprises from about 0.01% to about 10% of the polyorganosiloxane;
   c) from about 0.01% to about 10% of a silicone-polyoxyalkylene copolymer surfactant selected from the group consisting of silicone-linear polyoxyalkylene copolymers having the formula (I):

$$M'D_bD'_cM' \qquad (I)$$

wherein
   M' is a monofunctional unit $R_2R'SiO_{1/2}$;
   D is a difunctional unit $R_2SiO_{2/2}$;
   D' is a difunctional unit $RR'SiO_{2/2}$;
   R is independently H, $C_1$–$C_6$ alkyl, or aryl;
   R' is independently, an oxyalkylene containing moiety, H, or $CH_3$;
   b is an integer of from about 10 to about 1000; and
   c is an integer of from 0 to about 100, provided that when c is 0, at least one M' contains an oxyalkylene moiety; and silicone-graft polyoxyalkylene copolymers having the formula (II):

$$MD_bD'_cM \qquad (II)$$

wherein:
M is a monofunctional unit $R_3SiO_{1/2}$;
D is a difunctional unit $R_2SiO_{2/2}$;
D' is a difunctional unit $RR'SiO_{2/2}$;
R is independently H, $C_1$–$C_6$ alkyl, or aryl;
R' is an oxyalkylene containing moiety;
b is an integer of from about 10 to about 1000; and
c is an integer of from 1 to about 100; and
d) a carrier comprising:
   (i) at least about 0.5%, by weight of the composition, of a first solvent selected from the group consisting of water; water soluble organic solvents; organic solvents which are strongly to moderately strong in hydrogen-bonding parameter; and mixtures thereof; wherein the first solvent is other than a $C_1$–$C_3$ monohydric alcohol, a $C_1$–$C_3$ ketone and a $C_1$–$C_3$ ether.

2. The composition of claim 1 wherein the silicone-polyoxyalkylene copolymer surfactant has formula (I).

3. The composition of claim 2 wherein R' of said copolymer surfactant is an oxyalkylene containing moiety having the formula $$-R''(OC_nC_{2n})_y-R'''$$

wherein
R'' is a divalent radical for connecting the oxyalkylene portion of moiety R' to the siloxane backbone;
R''' is a terminating radical for the oxyalkylene portion of the moiety R';
n is an integer of from 2 to 4; and
y is an integer of 1 or greater, wherein the total from all the oxyalkylene units in the copolymer surfactant is about 10 or greater.

4. The composition of claim 3 wherein R'' has the formula $-(C_mH_{2m})-$, wherein m is an integer of from 2 to 8.

5. The composition of claim 4 wherein n is 2 or 3.

6. The composition of claim 5 wherein the oxyalkylene units of R' have an ethylene oxide unit (EO) to propylene oxide unit (PO) ratio of $EO_{10-100}PO_{0-100}$.

7. The composition of claim 6 wherein the oxyalkylene units of R' have an ethylene oxide unit (EO) to propylene oxide unit (PO) ratio of $EO_{20-70}PO_{20-70}$.

8. The composition of claim 7 wherein the oxyalkylene units of R' have an ethylene oxide unit (EO) to propylene oxide unit (PO) ratio of $EO_{30-70}PO_{30-70}$.

9. The composition of claim 6 wherein m is from 3 to 6.

10. The composition of claim 9 wherein c is 0.

11. The composition of claim 10 wherein b is from about 20 to about 200.

12. The composition of claim 5 wherein the block copolymer surfactant has the formula:

$$H[(OCHCH_3CH_2)_a(OCH_2CH_2)_b]_x(C_nH_{2n}) - \underset{\underset{CH_3}{|}}{\overset{\overset{CH_3}{|}}{Si}} - O)_w - \underset{\underset{CH_3}{|}}{\overset{\overset{CH_3}{|}}{Si}} - (C_nH_{2n})[(OCH_2CH_2)_b(OCHCH_3CH_2)_a]_xOH$$

wherein x is an integer of 1 or greater; n is an integer of from 2 to 4; a and b independently are an integer of from about 15 to about 30; and w is an integer of from about 20 to about 200.

13. The composition of claim 2 wherein the personal care composition comprises at least about 3%, by weight of the composition, of said first solvent; and at least about 40%, by weight of the composition, of a second solvent selected from the group consisting of $C_1$–$C_3$ monohydric alcohols, $C_1$–$C_3$ ketones, $C_1$–$C_3$ ethers, and mixtures thereof.

14. The composition of claim 13 wherein the second solvent is selected from monohydric alcohols.

15. The composition of claim 14 wherein the monohydric alcohol is selected from the group consisting of ethanol, n-propanol, isopropanol and mixtures thereof.

16. The composition of claim 14 wherein said first solvent is water.

17. The composition of claim 1 wherein the silicone-polyoxyalkylene copolymer surfactant has formula (II).

18. The composition of claim 17 wherein b is from about 100 to about 500 and c is from about 10 to about 50.

19. The composition of claim 17 wherein R' of said copolymer surfactant has the formula —R''(OC$_n$C$_{2n}$)$_y$—R''' wherein
R'' is a divalent radical for connecting the oxyalkylene portion of moiety R' to the siloxane backbone;
R''' is a terminating radical for the oxyalkylene portion of the moiety R';
n is an integer of from 2 to 3; and
y is an integer of 1 or greater.

20. The composition of claim 19 wherein R'' has the formula —(C$_m$H$_{2m}$)—, wherein m is an integer of from 2 to 8.

21. The composition of claim 20 wherein the oxyalkylene units of R' have an ethylene oxide unit (EO) to propylene oxide unit (PO) ratio of EO$_{10-100}$PO$_{0-100}$.

22. The composition of claim 21 wherein the oxyalkylene units of R' have an ethylene oxide unit (EO) to propylene oxide unit (PO) ratio of EO$_{10-30}$PO$_{1-30}$.

23. The composition of claim 17 wherein the carrier further comprises a second solvent selected from the group consisting of C$_1$–C$_3$ monohydric alcohols, C$_1$–C$_3$ ketones, C$_1$–C$_3$ ethers, and mixtures thereof.

24. The composition of claim 23 wherein the second solvent is selected from C$_1$–C$_3$ monohydric alcohols.

25. The composition of claim 24 wherein the monohydric alcohol is selected from the group consisting of ethanol, n-propanol, isopropanol and mixtures thereof.

26. The composition of claim 24 wherein said first solvent is water.

27. The composition of claim 1 wherein the hair styling polymer is selected from the group consisting of anionic polymers, cationic polymers, amphoteric polymers, non-ionic polymers, and mixtures thereof.

28. The composition of claim 27 wherein the hair styling polymer is selected from the group consisting of (i) linear, silicone block copolymers; (ii) silicone graft copolymers comprising a linear, non-silicone polymeric backbone having a silicone macromonomer side chain; (iii) silicone graft copolymers comprising a linear, silicone polymeric backbone having a non-silicone macromonomer side chain; and (iv) mixtures thereof.

29. The composition of claim 28 wherein the hair styling polymer is a silicone graft copolymer comprising a linear, non-silicone polymeric backbone having a silicone macromonomer side chain.

30. The composition of claim 1 wherein the average particle size of the dispersed polyorganosiloxane is about 60 nanometers or less.

31. The composition of claim 30 wherein the average particle size of the dispersed polyorganosiloxane is about 40 nanometers or less.

32. The composition of claim 1 wherein the first solvent is selected from the group consisting of water, propylene glycol, glycerine, phenoxyethanol, dipropylene glycol, sugars, dibutyl phthalate, propylene carbonate, propylene glycol monomethyl ether, methyl propionate, methyl acetate and mixtures thereof.

33. The composition of claim 1 wherein the first solvent is water.

34. A personal care composition suitable for styling hair formed by combining components comprising:
a) from about 0.01% to about 20% of a hair styling polymer;
b) a polyorganosiloxane emulsion comprising:
(i) a polyorganosiloxane dispersed as particles in the emulsion, the polyorganosiloxane having an average particle size of less than about 150 nanometers, and
(ii) a surfactant system for dispersing the organopolysiloxane in the emulsion,; wherein the amount of emulsion is such that the personal care composition comprises from about 0.01% to about 10% of the polyorganosiloxane;
c) from about 0.01% to about 10% of a silicone-polyoxyalkylene copolymer surfactant selected from the group consisting of silicone-linear polyoxyalkylene copolymers having the formula (I):

M'D$_b$D'$_c$M'   (I)

wherein
M' is a monofunctional unit R$_2$R'SiO$_{1/2}$;
D is a difunctional unit R$_2$SiO$_{2/2}$;
D' is a difunctional unit RR'SiO$_{2/2}$;
R is independently H, C$_1$–C$_6$ alkyl, or aryl;
R' is independently, an oxyalkylene containing moiety, H or CH$_3$;
b is an integer of from about 10 to about 1000; and
c is an integer of from 0 to about 100, provided that when c is 0, at least one M' contains an oxyalkylene moiety; and silicone-graft polyoxyalkylene copolymers having the formula (II):

MD$_b$D'$_c$M   (II)

wherein:
M is a monofunctional unit R$_3$SiO$_{1/2}$;
D is a difunctional unit R$_2$SiO$_{2/2}$;
D' is a difunctional unit RR'SiO$_{2/2}$;
R is independently H, C$_1$–C$_6$ alkyl, or aryl;
R' is an oxyalkylene containing moiety;
b is an integer of from about 10 to about 1000; and
c is an integer of from 1 to about 100; and
d) a carrier comprising:
(i) at least about 0.5%, by weight of the composition, of a first solvent selected from the group consisting of water; water soluble organic solvents; organic solvents which are strongly to moderately strong in hydrogen-bonding parameter; and mixtures thereof; wherein the first solvent is other than a C$_1$–C$_3$ monohydric alcohol, a C$_1$–C$_3$ ketone and a C$_1$–C$_3$ ether.

* * * * *